United States Patent
De Taboada et al.

(10) Patent No.: US 10,315,042 B2
(45) Date of Patent: Jun. 11, 2019

(54) DEVICE AND METHOD FOR PROVIDING A SYNERGISTIC COMBINATION OF PHOTOTHERAPY AND A NON-LIGHT ENERGY MODALITY TO THE BRAIN

(75) Inventors: Luis De Taboada, Carlsbad, CA (US); Jackson Streeter, Reno, NV (US)

(73) Assignee: Pthera LLC, Newark, DE (US)

( * ) Notice: Subject to any disclaimer, the term of this patent is extended or adjusted under 35 U.S.C. 154(b) by 106 days.

(21) Appl. No.: 13/111,840

(22) Filed: May 19, 2011

(65) Prior Publication Data
US 2012/0016174 A1  Jan. 19, 2012

Related U.S. Application Data

(63) Continuation-in-part of application No. 12/617,658, filed on Nov. 12, 2009, which is a continuation of
(Continued)

(51) Int. Cl.
*A61N 5/06* (2006.01)
*A61N 5/04* (2006.01)
(Continued)

(52) U.S. Cl.
CPC .......... *A61N 5/0613* (2013.01); *A61N 5/04* (2013.01); *A61F 2007/0002* (2013.01);
(Continued)

(58) Field of Classification Search
CPC .......... A61N 5/0613; A61N 5/04; A61N 1/40; A61N 2/002; A61N 2/006; A61N 5/0618; A61N 2005/007; A61N 2005/0602; A61N 2005/0647; A61N 2005/0652; A61N 2005/0654; A61N 2005/0659; A61N 2005/0662; A61N 2005/067; A61N 2007/0078; A61N 2007/0095; A61F 2007/0002
(Continued)

(56) References Cited

U.S. PATENT DOCUMENTS 4,870,969 A   10/1989 Swartz
4,873,981 A   10/1989 Abrams et al.
(Continued)

OTHER PUBLICATIONS

Belevich et al., "Exploring the proton pump mechanism of cytochrome c oxidase in real time," Proc. Nat'l Acad. Sci., Feb. 20, 2007, 104(8):2685-2690.
(Continued)

*Primary Examiner* — Aaron F Roane
(74) *Attorney, Agent, or Firm* — Fish & Richardson P.C.

(57) ABSTRACT

Systems and methods that could reduce the potential for side effects while delivering a reduced amount of light energy and non-light energy to a patient while providing a desired therapeutic effect that might otherwise only be achievable with a higher dose of either the light energy or non-light energy administered alone are disclosed. In certain embodiments, disclosed is a system and method for treating a patient, by administering a combination of light therapy from a light energy source in addition to one, two, or more other non-light energy modalities to a target region of a patient for a synergistic therapeutic effect.

16 Claims, 11 Drawing Sheets

Related U.S. Application Data application No. 11/482,220, filed on Jul. 7, 2006, which is a continuation of application No. 10/682,379, filed on Oct. 9, 2003, now Pat. No. 7,303,578, which is a continuation-in-part of application No. 10/287,432, filed on Nov. 1, 2002, now abandoned.

(60) Provisional application No. 61/346,420, filed on May 19, 2010, provisional application No. 60/442,693, filed on Jan. 24, 2003, provisional application No. 60/487,979, filed on Jul. 17, 2003, provisional application No. 60/502,147, filed on Sep. 11, 2003, provisional application No. 60/336,436, filed on Nov. 1, 2001, provisional application No. 60/369,260, filed on Apr. 2, 2002.

(51) Int. Cl.

| | | |
|---|---|---|
| A61F 7/00 | (2006.01) | |
| A61N 1/40 | (2006.01) | |
| A61N 2/00 | (2006.01) | |
| A61N 5/00 | (2006.01) | |
| A61N 5/067 | (2006.01) | |
| A61N 7/00 | (2006.01) | |

(52) U.S. Cl.
CPC ............... *A61N 1/40* (2013.01); *A61N 2/002* (2013.01); *A61N 2/006* (2013.01); *A61N 5/0618* (2013.01); *A61N 5/0622* (2013.01); *A61N 2005/007* (2013.01); *A61N 2005/0602* (2013.01); *A61N 2005/067* (2013.01); *A61N 2005/0647* (2013.01); *A61N 2005/0652* (2013.01); *A61N 2005/0654* (2013.01); *A61N 2005/0659* (2013.01); *A61N 2005/0662* (2013.01); *A61N 2007/0078* (2013.01); *A61N 2007/0095* (2013.01)

(58) Field of Classification Search
USPC .......................................................... 607/88
See application file for complete search history.

(56) References Cited

U.S. PATENT DOCUMENTS

| | | | |
|---|---|---|---|
| 5,054,470 A | 10/1991 | Fry et al. | |
| 5,725,471 A | 3/1998 | Davey et al. | |
| 5,989,245 A | 11/1999 | Prescott | |
| 6,042,531 A | 3/2000 | Holcomb | |
| 6,086,525 A | 7/2000 | Davey et al. | |
| 6,132,361 A | 10/2000 | Epstein et al. | |
| 6,425,852 B1 | 7/2002 | Epstein et al. | |
| 6,537,304 B1 | 3/2003 | Oron | |
| 6,770,031 B2 | 8/2004 | Hynynen et al. | |
| 6,918,922 B2 | 7/2005 | Oron | |
| 6,974,224 B2 | 12/2005 | Thomas-Benedict | |
| 7,303,578 B2 | 12/2007 | De Taboada et al. | |
| 2003/0216797 A1* | 11/2003 | Oron | A61N 5/0613 607/89 |
| 2005/0107851 A1 | 5/2005 | De Taboada et al. | |
| 2005/0165458 A1 | 7/2005 | Boveja et al. | |
| 2006/0184209 A1 | 8/2006 | John et al. | |
| 2007/0066996 A1* | 3/2007 | Katzman | A61K 31/165 607/3 |
| 2007/0129776 A1 | 6/2007 | Robins et al. | |
| 2007/0179570 A1 | 8/2007 | De Taboada et al. | |
| 2007/0239235 A1* | 10/2007 | DiMauro | A61N 5/0601 607/88 |
| 2009/0254154 A1 | 10/2009 | De Taboada et al. | |
| 2010/0211136 A1 | 8/2010 | De Taboada et al. | |

OTHER PUBLICATIONS

Belevich et al., "Protoncoupled electron transfer drives the proton pump of cytochrome c oxidase," Nature, Apr. 2006, 440(7085):829-832.

Friedmann et al, "Combined Magnetic and Pulsed Laser Fields Produce Synergistic Acceleration of Cellular Electron Transfer." Laser Therapy [Retrieved from the Internet] URL<https://www.jstage.jst.go.jp/article/islsm/18/3/18_3_137/_article>. 2009, 18(3):137-141.

Karu et al., "Cell Attachment to Extracellular Matrices is Modulated by Pulsed Radiation at 820 nm and Chemicals that Modify the Activity of Enzymes in the Plasma Membrane," Lasers in Surgery and Medicine, Sep. 2001, 29(3):274-281.

Kubsik et al., "Application of laser radiation and magnetostimulation in therapy of patients with multiple sclerosis." NeuroRehabilitation, Jan. 1, 2016, 38(2):183-90.

Lepselter et al., "Biological and clinical aspects in laser hair removal," J. Dermatological Treatment, Apr. 1, 2004, 15(2):72-83.

Lisman et al., "Two Light-Induced Processes in the Photoreceptor Cells of Limulus Ventral Eye," J. Gen. Physiology, Nov. 1, 1971, 58(5):544-561.

Murugan et al., "Synergistic interactions between temporal coupling of complex light and magnetic pulses upon melanoma cell proliferation and planarian regeneration." Electromagnetic biology and medicine, Apr. 3, 2017, 36(2):141-8.

Tuchin, "Tissue Optics: Light Scattering Methods and Instruments for Medical Diagnosis," SPIE Press (2000), Bellingham, WA, pp. 3-11.

Wells et al., "Biophysical mechanisms responsible for pulsed low-level laser excitation of neural tissue," Proc. SPIE, Mar. 1, 2006, 6084:60840X1-7.

Wells et al., "Pulsed Laser versus Electrical Energy for Peripheral Nerve Stimulation," J. Neurosci. Methods, Jul. 30, 2017 163(2):326-337.

\* cited by examiner

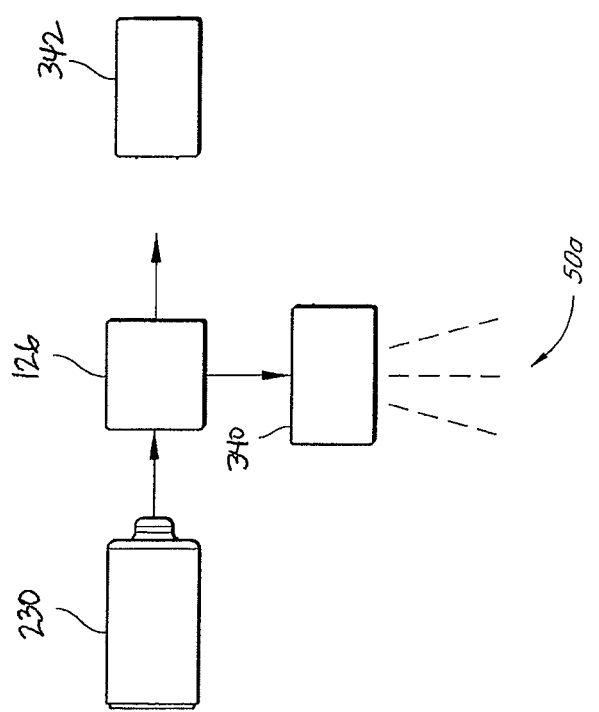

DEVICE AND METHOD FOR PROVIDING A SYNERGISTIC COMBINATION OF PHOTOTHERAPY AND A NON-LIGHT ENERGY MODALITY TO THE BRAIN

PRIORITY CLAIM

The present application claims priority under 35 U.S.C. § 119(e) as a nonprovisional application of U.S. Prov. Pat. App. No. 61/346,420 filed on May 19, 2010, and hereby incorporated by reference in its entirety. The present application also claims priority under 35 U.S.C. § 120 as a continuation-in-part application of U.S. patent application Ser. No. 12/617,658 filed on Nov. 12, 2009, which is a continuation of U.S. patent application Ser. No. 11/482,220, filed Jul. 7, 2006, which is a continuation of U.S. patent application Ser. No. 10/682,379, filed Oct. 9, 2003 and issued Dec. 4, 2007 as U.S. Pat. No. 7,303,578, and which claims benefit to U.S. Provisional Application No. 60/442,693, filed Jan. 24, 2003, U.S. Provisional Application No. 60/487,979, filed Jul. 17, 2003, and U.S. Provisional Application No. 60/502,147, filed Sep. 11, 2003, and which is a continuation-in-part of U.S. patent application Ser. No. 10/287,432, filed Nov. 1, 2002 and now abandoned, which claims benefit to U.S. Provisional Application No. 60/336,436, filed Nov. 1, 2001 and U.S. Provisional Application No. 60/369,260, filed Apr. 2, 2002, all of which are hereby incorporated by reference in their entireties.

BACKGROUND

A variety of energy modalities are known and have been used to treat various medical conditions. However, administration of relatively high doses of energy to a patient increases the risk for potential side effects.

SUMMARY

Disclosed herein is a method for treating a patient, including the steps of administering to the patient an amount of light energy, and an amount of non-light energy. In some embodiments, the time-averaged irradiance of light energy at the target tissue administered is less than about 100 mW/cm$^2$. In some embodiments, the amount of non-light energy is a subtherapeutic amount of energy. The light energy and non-light energy could be delivered to any desired anatomical location, such as the patient's brain. In some embodiments, the light energy and non-light energy are administered concurrently. In other embodiments, at least a portion of the light energy is administered prior to, or following the administration of non-light energy, or in alternating pulses in some embodiments. The non-light energy could be, for example, magnetic energy such as trans-cranial magnetic stimulation, acoustic energy, radiofrequency energy, microwave energy, or thermal energy. The light energy could have, in some embodiments, a wavelength between about 630 nanometers to about 1064 nanometers, between about 730 nanometers to about 840 nanometers, or between about 730 nanometers and about 750 nanometers. The target tissue could be, for example, ischemic brain tissue, muscle tissue, peripheral nerve tissue, bone tissue, cancerous tissue, or a wide variety of other tissues depending on the desired clinical result.

Also disclosed herein is a method for treating a patient, including the steps of administering to the patient an amount of light energy; and administering to the patient an amount of non-light energy, wherein the combination of the amount of light energy and the amount of non-light energy produce a treatment effect to the patient, wherein the amount of light energy administered is at least about 10% less than an amount of light which would produce the same treatment effect to the patient without administering to the patient the amount of non-light energy.

Also disclosed herein is a method for treating a patient, including the steps of administering to the patient an amount of light energy; and administering to the patient an amount of non-light energy, wherein the combination of the amount of light energy and the amount of non-light energy produce an efficacious treatment effect to the patient, wherein the amount of light energy administered is insufficient to produce the efficacious treatment effect to the patient without administering to the patient the amount of non-light energy. In some embodiments, the efficacious treatment effect is improvement of neurologic function, reduction of pain, or reduction in size of a tumor.

In another aspect, disclosed herein is a system for delivery light energy and non-light energy to a patient. The system includes a light energy source. In some embodiments, the light energy source can be configured to deliver time-averaged irradiance of light energy at a target tissue that is less than about 100 mW/cm$^2$. In some embodiments, the light source is configured to deliver light having a wavelength between about 630 nanometers to about 1064 nanometers, between about 730 nanometers to about 840 nanometers, or between about 730 nanometers and about 750 nanometers.

The system can also include a non-light energy source, and a controller operably connected to both the light energy source and the non-light energy source. The controller can be configured such that the system provides light energy and non-light energy to produce a treatment effect to the patient, wherein the amount of light energy administered is at least about 10% less than an amount of light which would produce the same treatment effect to the patient without administering to the patient the amount of non-light energy. In some embodiments, the amount of non-light energy is a subtherapeutic amount of energy. The controller can be configured such that the light energy and the non-light energy are administered concurrently. In some embodiments, the controller is configured such that at least a portion of the light energy is administered prior to, during, or after the administration of the non-light energy. In some embodiments, the non-light energy source is configured to deliver one or more of the following: magnetic energy (including trans-cranial magnetic stimulation), acoustic energy, radiofrequency energy, microwave energy, or thermal energy.

BRIEF DESCRIPTION OF THE DRAWINGS

FIG. 5 is a block diagram of a programmable controller for controlling one or more energy sources, in accordance with certain embodiments described herein.

DETAILED DESCRIPTION

Combination Therapy

Figure 1A:
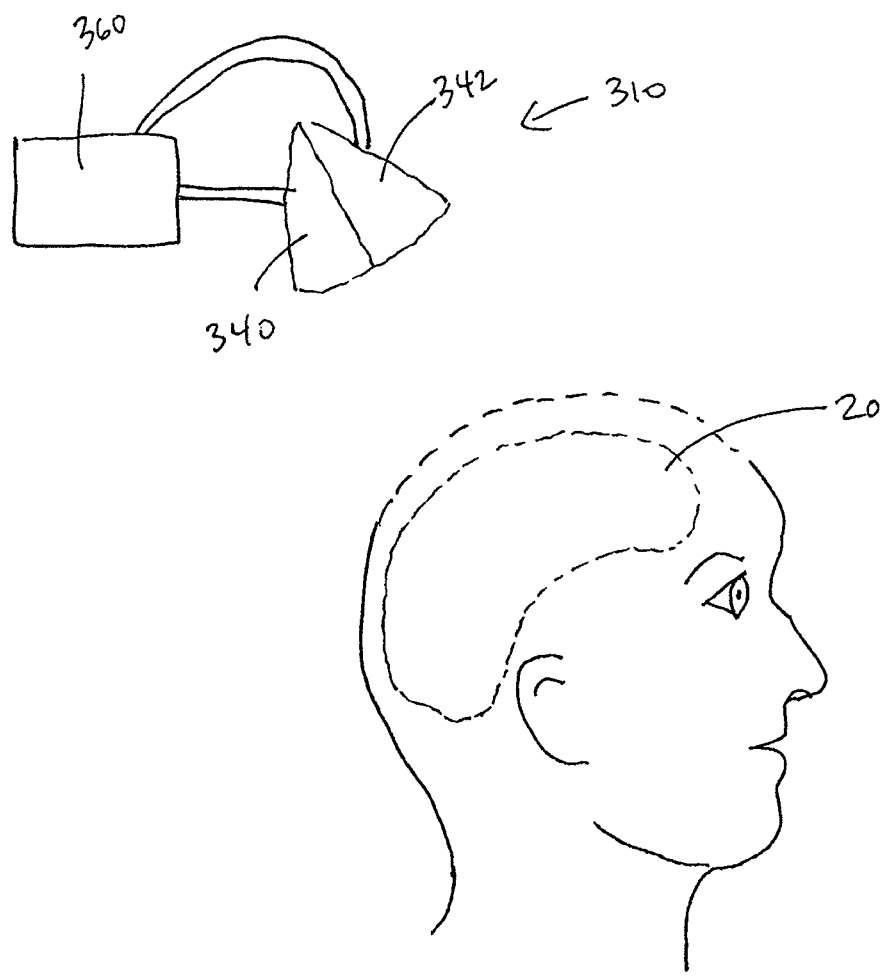
FIG. 1A depicts one example of a multi-modality therapy apparatus that includes a light source and a non-light energy source for treating a patient.

Certain embodiments described herein advantageously provide systems and methods that could reduce the potential for side effects while delivering a reduced amount of light energy and non-light energy to a patient while providing a desired therapeutic effect that might otherwise only be achievable with a higher dose of either the light energy or non-light energy administered alone. In certain embodiments, disclosed is a method for treating a patient, by administering a combination of light therapy in addition to one, two, or more other non-light energy modalities to a target region of a patient for a synergistic therapeutic effect. In some embodiments, either the light therapy, the other non-light energy modality therapy, or both therapies may provide a therapeutic effect when administered separately, but have an enhanced therapeutic effect when administered in a combination therapeutic regimen. For example, in one embodiment where the light therapy has a first therapeutic effect and the non-light therapy has a second therapeutic effect, the combination therapeutic effect has a third therapeutic effect that is greater than the sum of the first and second therapeutic effects.

In some circumstances, there is a correlation between the amount of energy delivered for a therapeutic purpose and the degree of therapeutic effect on a patient. However, in some circumstances, delivering greater amounts of energy could increase the risk of undesirable side effects related to the energy delivery. Thus, it would be desirable, in some embodiments, if the dose, duration of therapy, or other parameter of either the light or non-light energy modality therapy used to achieve a particular therapeutic effect could be reduced when the light therapy and the non-light therapy are administered in combination to provide a synergistic therapeutic effect while also resulting in relatively less side effects as compared to the dose, duration of therapy, or other parameter when the light or non-light energy modality therapy are used in combination with one another. In some embodiments, either the light therapy, the non-light energy modality therapy, or both therapies may have no therapeutic effect (e.g., if a subtherapeutic dose of energy is administered), a minimal therapeutic effect, a different therapeutic effect, or a reduced therapeutic effect when administered alone, but have an enhanced, different, or more desirable therapeutic effect when administered as part of a combination therapeutic regimen. Without being bound by theory, administering relatively lower therapeutic doses or even subtherapeutic (having no therapeutic effect) doses of a plurality of energy modalities can advantageously produce a desired treatment effect with less potential side effects compared with a treatment regimen including therapeutic doses of each separate energy modality. For example, not to be limited by theory, but administration of light energy to a patient prior to administration of non-light energy to the patient could "prime" or sensitize the region to be treated such that less non-light energy can be used to produce the desired treatment effect.

In some embodiments, the total dosage of either the light therapy, the non-light energy modality therapy, or both used to achieve a desired therapeutic effect when the light therapy and non-light therapy are administered in a combination regimen is at least about 5%, 10%, 15%, 20%, 25%, 30%, 40%, 50%, 60%, 70%, 80%, or 90% less than the dose used to achieve the same therapeutic effect when either the light therapy or the non-light energy modality therapy are administered alone.

Non-Light Energy Modalities

The one, two, or more non-light energy modalities can be, for example, electromagnetic energy, such as RF, microwave energy, and magnetic energy; ultrasound energy such as high-intensity focused ultrasound energy; mechanical energy, electrical therapy (e.g., low level electrical current therapy), thermal energy, or cooling (e.g., cryotherapy).

FIG. 1A schematically illustrates an embodiment of a multi-modality energy therapy system. The therapy apparatus 310 includes a light source 340 (e.g., a light source external to the patient's body) adapted to irradiate a portion of the patient's brain 20 with a selected power density and wavelength of light. The therapy apparatus 310 also includes one, two, or more non-light energy sources 342 (e.g., non-light sources external to, or even implanted within the patient's body) adapted to irradiate a portion of the patient's brain 20, such that the combination of the light source 340 and the non-light source 342 results in an efficacious therapeutic effect. The therapy apparatus 310 can further include one, two, or more controllers 360 for energizing the light source 340 and the non-light energy source 342 as to selectively produce one, two, or more different irradiation patterns (e.g., spatial irradiation patterns, temporal irradiation patterns). The controller 360 of certain embodiments is configured to adjust one, two, or more parameters of the light source 340 and the non-light energy source 342, including timing and duration of treatment (e.g., concurrent light and non-light energy delivery, sequential delivery, overlapping delivery, etc.). In some embodiments, the light source 340 and non-light energy source 342 are provided in separate therapy apparatuses 342 rather than integrated together as shown.

In some embodiments, the system includes a plurality of controllers 360, e.g., separate controllers for the light energy source 340 and the non-light energy source 342. The energy from the non-light energy source 342 can be at various intensities, frequencies, wave forms (e.g., square waves, triangle waves, sinusoidal waves, and/or saw-tooth waves), square wave pulse trains, trigonometric wave pulse trains, sinusoidal wave pulse trains, and other types of wave trains suitable for treating a subject. The devices can be fixed or variable (e.g., incorporating one, two, or more parameters such as frequencies, wave forms, etc.) mode devices depending on the treatment procedure.

The non-light energy source 342 can include, without limitation, one or more transducers, such as acoustic transducers, ultrasound transducers, magnetic transducers, electro-magnetic transducers, pressure transducers (e.g., mechanical impulse transducers), and other types of transducers suitable for use on a subject. The transducers can be energized to output penetrating energy that causes cell stimulation or activation. The non-light energy delivery system, in some embodiments, may be a field generator (e.g., an electro-magnetic field generator), radiofrequency emitter, vibrator (e.g., an unbalanced mass vibration system), electrical stimulator (e.g., electrical stimulators configured selectively output low levels to high levels of electrical currents), magnetic stimulator, and the like.

Further details regarding examples of non-light delivery systems and methods are disclosed below.

Electromagnetic Energy Therapy

Figure 1B:
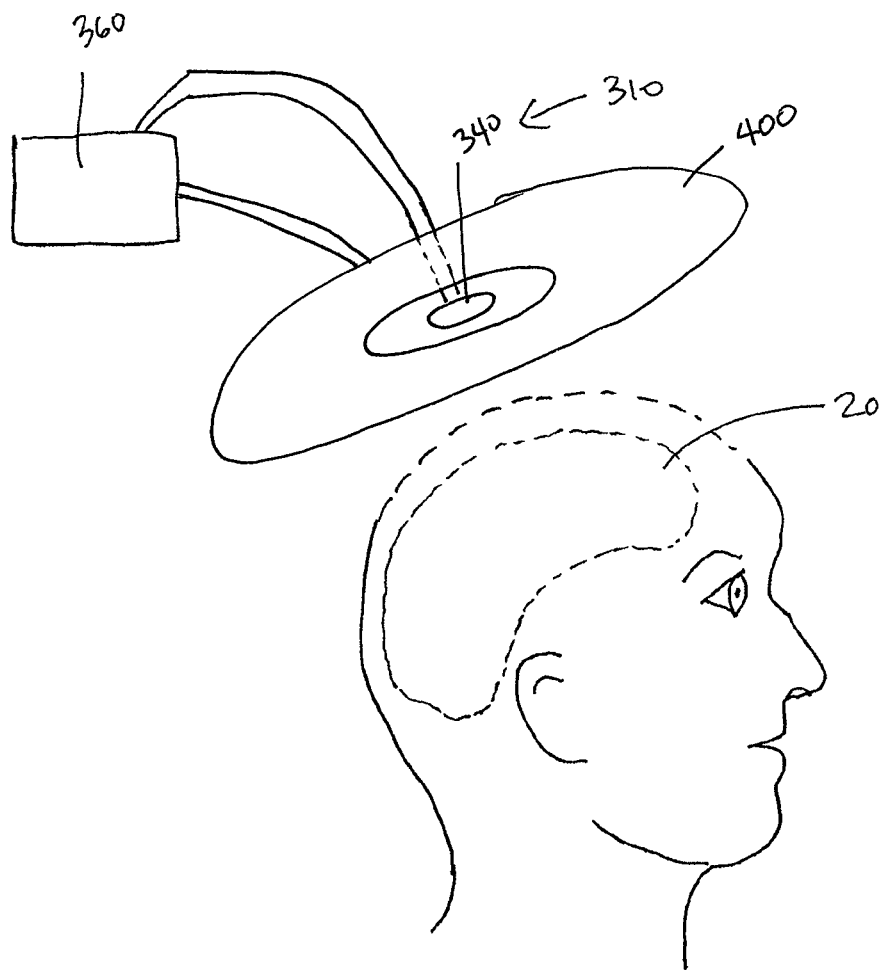
FIG. 1B depicts one example of a multi-modality therapy apparatus that includes a light source and a magnetic energy source for treating a patient.

In some embodiments, light therapy can be combined with magnetic energy therapy, such as transcranial magnetic stimulation (TMS). FIG. 1B schematically illustrates a multi-modality energy therapy system similar to that illustrated in FIG. 1A, with the non-light energy source including a magnetic core 400 for the delivery of magnetic energy, along with a light energy source 340 such as a laser diode having a distal end that is coaxial with an central aperture of the magnetic core 400.

TMS can be delivered at any appropriate frequency, such as between about 0.1 Hz and 20 Hz, or about 1 Hz and 10 Hz in some embodiments. The stimulation could be paired-pulse, biphasic, monophasic, or repetitive TMS (rTMS). The average magnetic field utilized could be, for example, between about 0.25 and 4 Teslas, such as between about 0.5 and 2 Teslas. In some embodiments, the peak field could be significantly higher, such as at least 5 Teslas, 10 Teslas, or more with a relatively short pulse duration. In some embodiments, the magnetic field intensity utilized is less than about 150%, 140%, 130%, 120%, 110%, 100%, 95%. 90%, 85%, 80%, 75%, 70%, 65%, 60%, 55%, 50%, 45%, 40%, 35%, 30%, 25%, 20%, or less than the patient's observed resting motor threshold. The resting motor threshold is the minimum intensity of stimulation necessary to elicit a motor evoked potential (which may be, in some embodiments, at least about 10, 25, 50, 75, 100 or more microvolts) in 50% of trials in a target muscle using a single TMS pulse. Patients could be treated for 50, 45, 40, 35, 30, 25, 20, 15, 10, 5, 4, 3, 2, or less sessions, and receive less than about 4,000, 3,500, 3,000, 2,500, 2,000, 1,500, 1000, 800, 600, 400, 200, or less pulses per session. Each pulse could last, for example, between about 1 and 1,000 milliseconds, or less than about 1,000, 500, 100, 50, or 10 milliseconds in some embodiments, or between 2 and 10 milliseconds in other embodiments. In some embodiments, the duty cycle of the TMS portion, and/or the entire device could be no more than 100%, 90%, 80%, 70%, 60%, 40%, 40%, 30%, 20%, 10%, 5%, or less. In some embodiments, the TMS or rTMS could include systems and methods as described in U.S. Pat. Nos. 5,725,471 and 6,086,525 to Davey et al.; and U.S. Pat. Nos. 6,132,361 and 6,425,852 to Epstein et al.; all of which are hereby incorporated by reference in their entireties. In other embodiments, the multi-modality therapy can also include systems for electromagnetic treatment, e.g., as described in U.S. Pat. No. 6,042,531 issued to Holcomb, which is incorporated in its entirety by reference herein, or the NeuroStar® TMS Therapy System by Neuronetics, Inc. (Malvern, Pa.).

Figure 2:
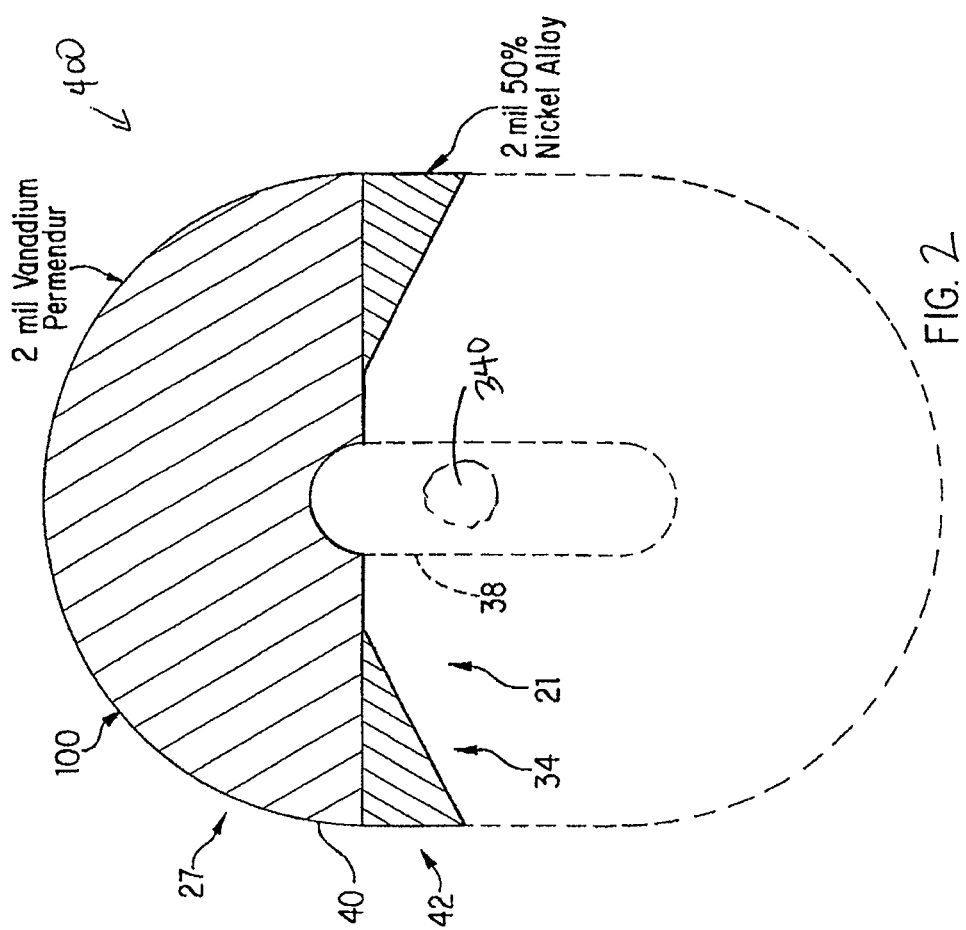
FIG. 2 illustrates one example of a multi-modality therapy apparatus that includes a light source and a non-light energy source for treating a patient, where the non-light energy source is a magnetic core.

One embodiment of a multi-modality treatment system 400 including a light source 340 (e.g., a laser diode) and a magnetic stimulator core 27 is schematically illustrated in FIG. 2. In some embodiments, the light source 340 could be advantageously positioned within a central aperture of the core 27 as illustrated, and have a distal end that is longitudinally in the same plane as the core 27, or proximally or distally offset from the longitudinal plane of the core 27. The core 27 is made of a magnetic material, such as a ferromagnetic material. In some embodiments, the material of the core has a magnetic saturability of at least 0.5 Tesla. Higher saturabilities can also be used, such as with saturabilities of at least 1.5 Tesla or higher, or even 2.0 Tesla or higher could be used in some embodiments. Non-limiting possible materials for the core include vanadium permendur or 3% grain oriented steel. As shown in FIG. 2, in one embodiment, core 27 is cut from an oval winding of 2 mil vanadium permendur. Two, three, or more cores can, in fact, be cut from a single oval winding, by cutting one core from each side of the oval. For illustration purposes, only a single core is shown in the diagram of FIG. 2. In some embodiments, a typical core can be wound using two mil stock of vanadium permendur. A long ribbon of such material is wound on a mandrel (e.g. a mandrel of wood or plastic) for the radius, thickness and depth desired. Each side of the ribbon is coated with a thin insulative coating to electrically isolate it from its neighbor. After cutting the core from the entire oval winding, a potential core might span an angle of approximately 208 degrees, or in the range of about 205-215 degrees. One method of construction of such a core is described, for example, in U.S. Pat. No. 5,725,471, hereby incorporated by reference in its entirety. Some cores can be constructed from thin laminate, highly saturable material (i.e. materials with a saturability of at least 1.5-2.0 Tesla, although less saturable materials with a saturability of 0.5 Tesla and higher can be used as well). As an alternative to cutting the core as one entire section, the core can be cut as a semi-circular section 30 (see, e.g., FIG. 2). In this method of manufacture, the small sections 34 (e.g., triangular, circular, or wedge-shaped sections) at the bottom of the core are then cut separately, and attached to the semicircular section as shown in FIG. 2. In some embodiments, the smaller sections are also made from vanadium permendur. If necessary, however, the sections can be any material or alloy that has a saturation of at least 0.5 Tesla, and which can be worked by one of ordinary skill in the art. A suitable alloy for the sections 34, for example, is 2 mil 50% nickel alloy.

As shown in FIG. 2, in one embodiment, core 27 has an outer diameter of approximately 4.75 inches. The core 27 has an inner semi-circular aperture 38 at the center of the core 27. Inner semicircle 38 has a diameter of approximately 0.75 inches. In a version where the smaller sections are separate, triangular sections or wedges 34 are attached to the larger semi-circular section 30. Sections 34 have a length on the longer side 40, in contact with semi-circular section 30, of approximately 1.375 inches, and a length of approximately 0.75 inches on the shorter side 42 which is approximately coplanar with the outside of semi-circular section 30. In some embodiments, the cross sectional width of core 27 is approximately 0.625 inches. Various other dimensions for the core are also possible depending on the desired clinical result. Further details of embodiments of the light source 340 are described further in the application below. Treatment with light energy in combination with magnetic energy therapy can produce a synergistic result and decrease, for example, the field intensity, number of pulses, pulse time, duty cycle, or other parameter of the magnetic energy therapy and as such reduce the potential risk of side effects.

Figure 2A:
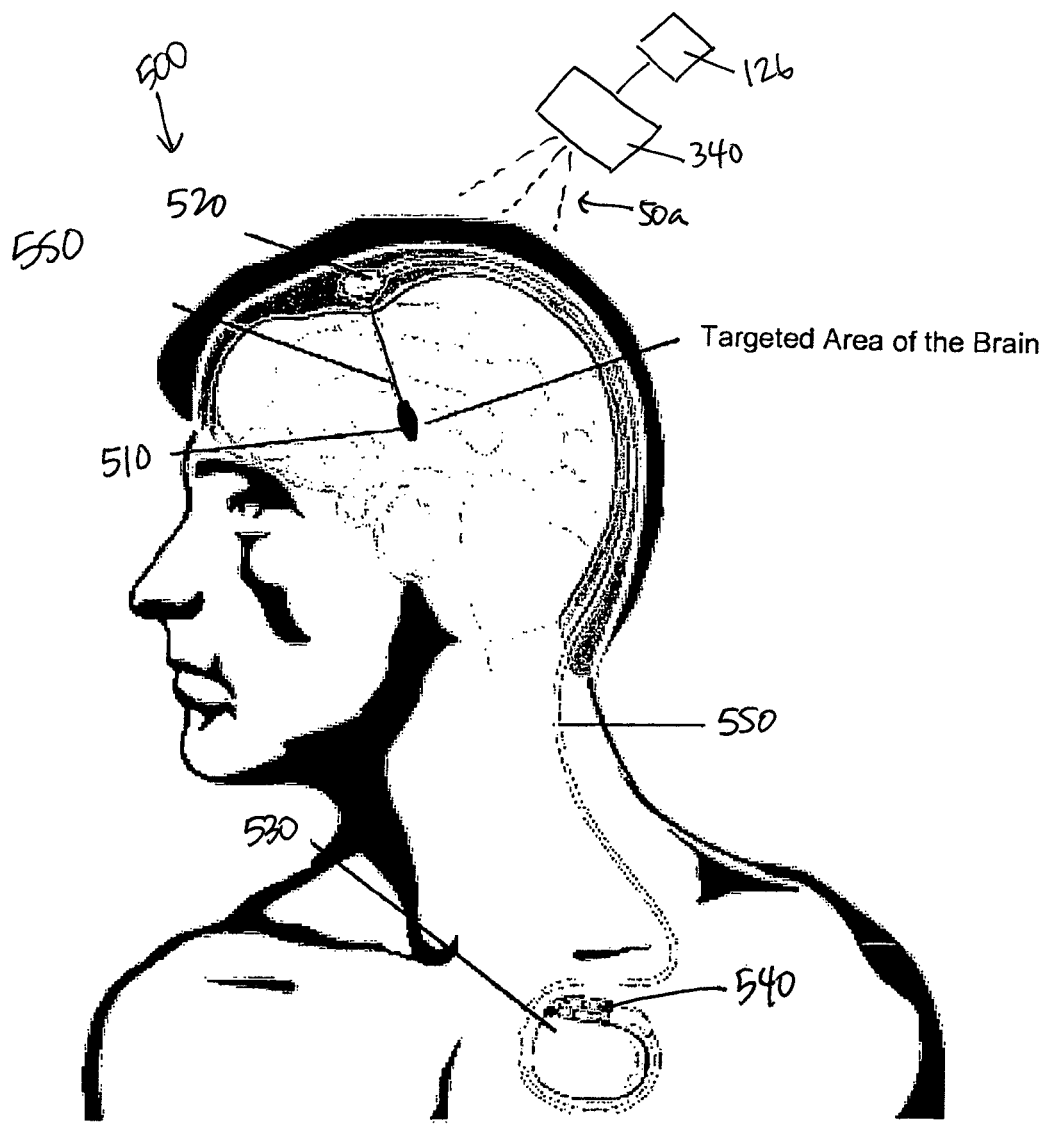
FIGS. 2A-2B illustrates one example of a multi-modality therapy apparatus that includes a light source and a non-light energy source for treating a patient, where the non-light energy source is an RF energy source.
Figure 2B:
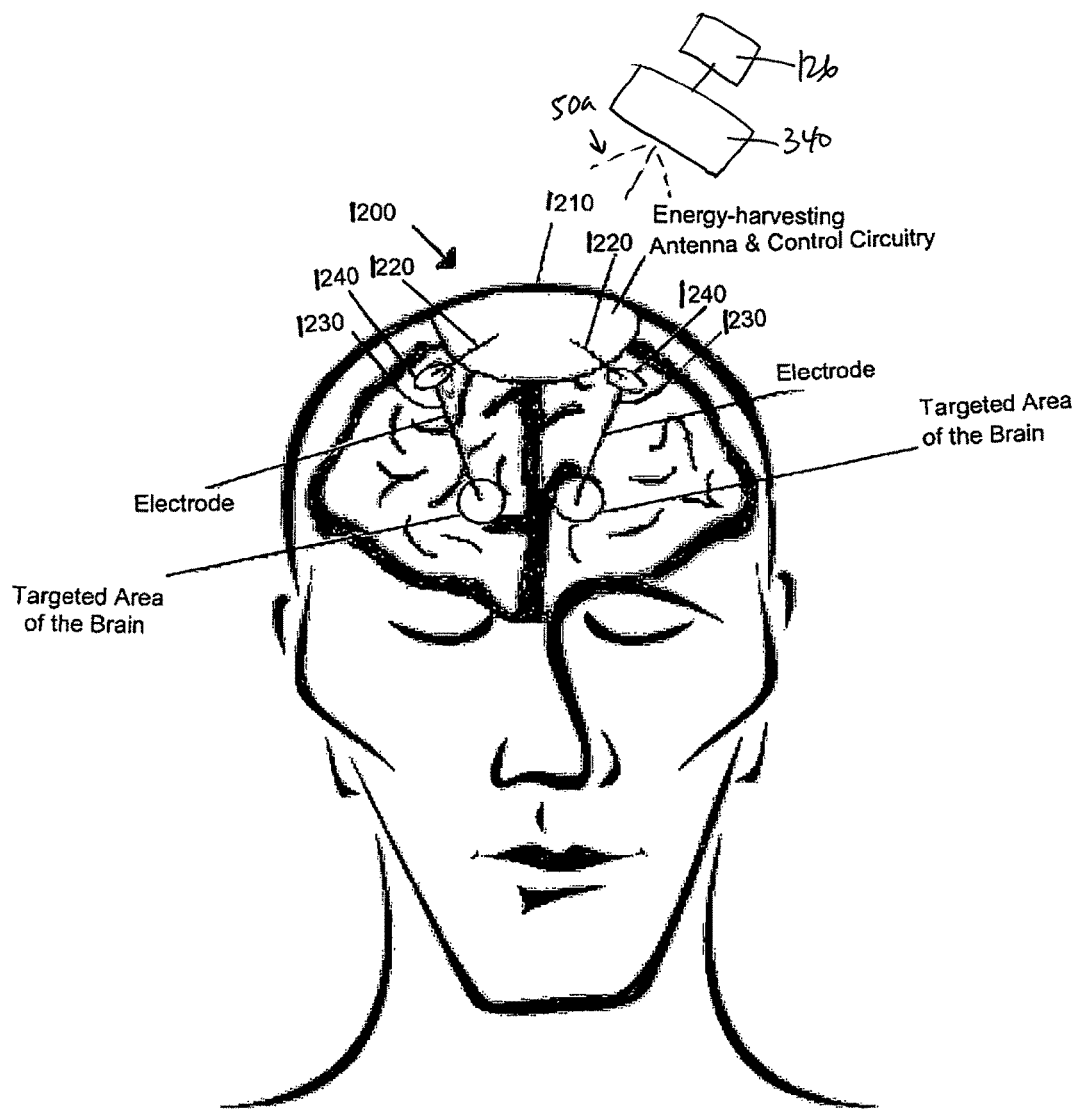

In still other embodiments, the multi-modality therapy could include radiofrequency (RF) or microwave therapy. As illustrated schematically in FIG. 2A, an RF device 500 could be implanted under the human scalp to treat the desired targeted area of the brain, including the cortical region or the deep brain region. The device 500 could include a pulse generator 540, at least one monopolar or bipolar electrode array 510 comprising one, two, three, four, five, six, or more electrodes connected by electrode lead(s) 550 to the skull by a securement device 520. The leads 510 can be connected to a neurostimulator 530 powered by a power source 540, such as a battery. The neurostimulator could have a discrete controller or communicate, such as wirelessly, with an external controller 126 that can also be configured to control a light source 340 for delivering light energy 50a to a patient. The power source 530 in some embodiments could be external to the patient and transmit energy to an energy (e.g., RF) receiving power circuit via inductive coupling. The pulse generator 540 can be placed subcutaneously just below the clavicle as illustrated in FIG. 2A, or another location such as under the scalp as illustrated in FIG. 2B, and can stimulate one, two, or more of the electrodes 510 present. The parameters of the device 500 and the stimulating current (voltage, frequency, pulse width, etc.) can be adjusted according to the desired clinical result. In some embodiments, the pulsing frequency may be between about 100 Hz and 500 Hz, such as between about 150 Hz and 250 Hz, or between about 160 Hz and 200 Hz. The pulse width could be, in some embodiments, between about 30 microseconds and about 240 microseconds, such as between about 60 microseconds and about 180 microseconds, or less than about 180, 150, 120, 90, 60, 45, 30, or less microseconds. The amplitude of stimulation could be less than about 5, 4.5, 4, 3.5, 3, 2.5, 2, 1.5, 1, 0.5, or less volts in some embodiments. The RF energy component could include features present, for example, in U.S. Pat. Pub. No. 2006/0184209 to John et al., which is hereby incorporated by reference in its entirety.

Referring back to FIG. 2B, a multi-modality system including a device for deep brain stimulation using RF energy harvesting 1200 is shown implanted under a human scalp. A flexible, implantable disc-shaped portion 1210 having a diameter of about 6 cm and a thickness of between 3 and 4 mm in some embodiments may be formed of a biocompatible material and include circuitry as further described herein. Lead wires 1220 may lead from the circuitry and be coupled to electrodes 1230 disposed in targeted areas of the brain. Electrodes 1230 may include conventional electrodes used for DBS. Neurostimulation lead securement devices 1240 including burr hole caps may serve to secure the lead wires 1220 to the electrodes. The circuitry may be operable to harvest and store RF energy, control the operation of the device 1200 and provide neurostimulation pulses and signals to the targeted areas of the brain. As in FIG. 2A, the RF component could have a discrete controller or communicate, such as wirelessly, with an external controller 126 that can also be configured to control a light source 340 for delivering light energy 50a to a patient. For a multi-modality system with a microwave rather than an RF energy component, one or more microwave antennas would be present rather than the electrodes, and a microwave generator would be present rather than an RF power source. In some embodiments, the microwave energy source may be configured to deliver less than about 600, 500, 400, 300, 200, 100, 90, 80, 70, 60, 50, 40, 30, 20, 10, 5, 3, 2, 1, or less joules/cm$^2$ to the target tissue in a treatment session.

Figure 2D:
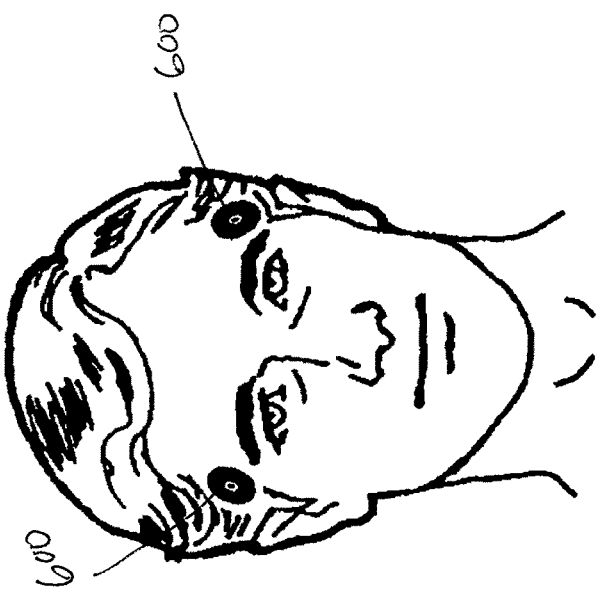
FIGS. 2C-2D illustrates one example of a multi-modality therapy apparatus that includes a light source and a non-light energy source for treating a patient, where the non-light energy source is configured for electroconvulsive therapy.
Figure 2C:
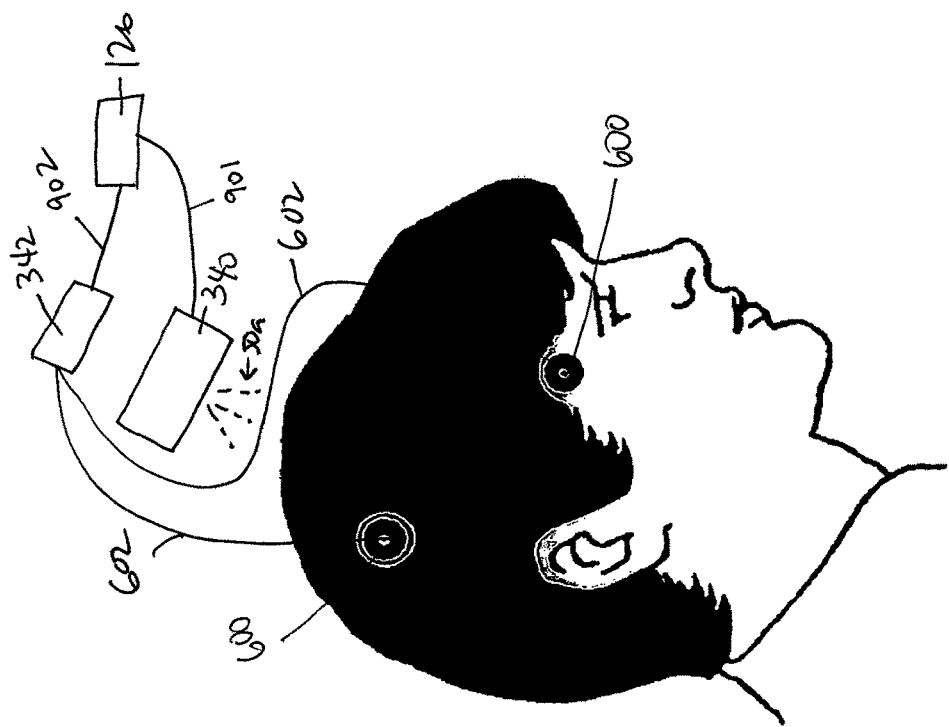

In some embodiments, light therapy can be combined with electrical stimulation therapy, such as electroconvulsive therapy (ECT), such as applying a stimulus to the surface of the scalp via electrodes, or more invasively such as directly to tissue such as brain tissue in some embodiments. FIG. 2C illustrates schematically one embodiment of unilateral nondominant or dominant electrode 600 placement for ECT, with electrodes 600 connected via wired or wireless leads 602 to stimulator 342 which is in turn connected either via a wired or wireless conduit 902 to controller 126, which is also operably connected to light source 340 configured to transmit light energy 50a to the patient as described elsewhere herein. FIG. 2D illustrates schematically one embodiment of bilateral electrode 600 placement, with the other elements illustrated in FIG. 2C omitted for clarity.

In some embodiments, the stimulus could be, for example, no more than about 100%, 75%, 50%, 25%, 10%, or less above the seizure threshold (which would result in induction of a seizure), or even below the seizure threshold in some embodiments. The total charge per treatment session could be, for example, no more than about 120, 115, 110, 105, 100, 95, 90, 85, 80, 75, 70, 65, 60, 55, 50, 45, 40, 35, 30, 25, 20, 15, 10, 5, or less millicoulombs (mC). The pulse amplitude could be no more than about 900, 800, 700, 600, 500, 400, 300, 200, 100, or less mA. The pulse shape could be, for example, rectangular or sinusoidal and monophasic or biphasic. The pulse width could be no more than about 2, 1.8, 1.6, 1.4, 1.2, 1.0, 0.8, 0.6, 0.4, 0.2, or less milliseconds (ms). The stimulus frequency could be, in some embodiments, less than about 500, 250, 200, 150, 100, 75, 50, 40, 30, 20, 15, 10, 5, 4, 3, 2, 1, 0.5, 0.2, or 0.1 pps. The number of pulses delivered in total to the patient per treatment session could be between about 250 and 5000, between about 1000 and 3000, at least about 250, 500, 1000, 2000, 3000, 4000, 5000, or no more than about 5000, 4000, 3000, 2000, 1000, 500, or 250 in other embodiments. Conventionally, a relatively low total charge or other ECT associated parameter was considered to be ineffective in treatment. However, not to be limited by therapy, combination therapy with light energy, e.g., prior to or during ECT treatment could reduce the total charge used and thus the associated side effects and/or risk of complications. In some embodiments, systems and methods such as described in U.S. Pat. Pub. No. 2005/0165458 A1 to Boveja et al., U.S. Pat. No. 4,873,981 to Abrams et al., or U.S. Pat. No. 4,870,969 to Swartz et al., hereby incorporated by reference in their entireties, could be utilized as the non-light energy sources.

Ultrasound Therapy

As another example, treatment can comprise directing a power density of light through the scalp of the patient to a target area of the brain concurrently with applying an amount of ultrasonic energy to the brain, the combined therapy of which results in an efficacious effect. Such a system can include systems for ultrasonic treatment, e.g., as described in U.S. Pat. No. 5,054,470 issued to Fry et al. or U.S. Pat. No. 6,770,031 to Hynynen et al., which are incorporated in their entireties by reference herein. The ultrasound beam can be focused in any desired fashion, such as, for example, geometrically, for example with a lens or with a spherically curved transducer, or electronically, by adjusting the relative phases of elements in an array of transducers (a "phased array"). By dynamically adjusting the electronic signals to the elements of a phased array, the beam can be steered to different locations, and aberrations due to tissue structures can be corrected.

Figure 2E:
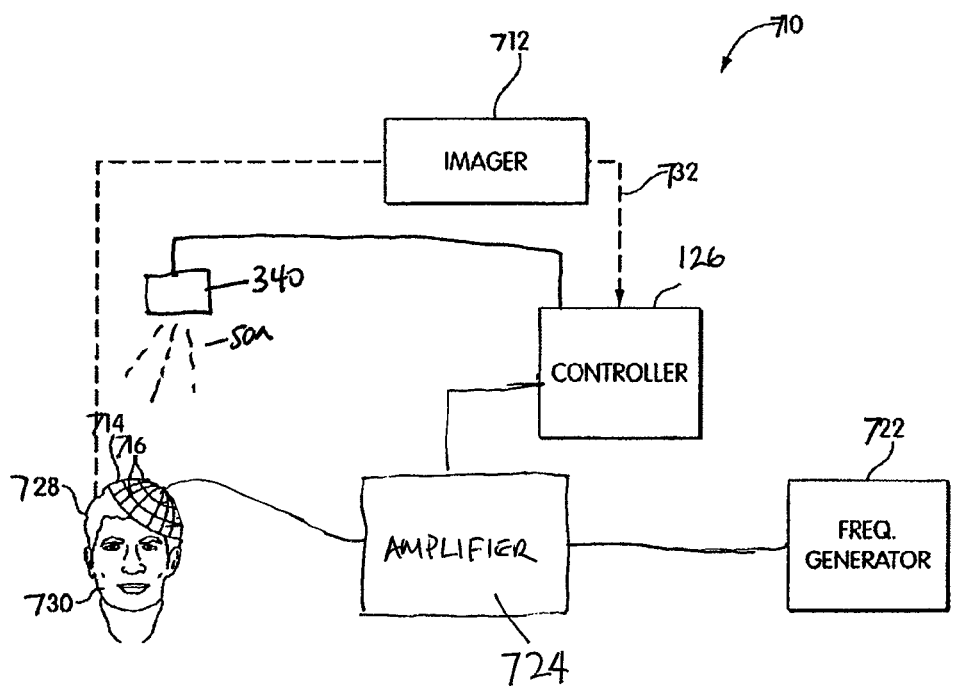
FIG. 2E illustrates one example of a multi-modality therapy apparatus that includes a light source and a non-light energy source for treating a patient, where the non-light energy source is an acoustic energy source.

FIG. 2E schematically illustrates one embodiment of a combination ultrasound-light therapy treatment system 710. The system includes a controller 126 for controlling light energy 50a delivery from the light source 340 as well as ultrasound energy delivery from amplifier 724 to a patient 730. In some embodiments, the system 710 could have separate controllers for the light source 340 and the amplifier 724. Amplifier 724 can be operably connected to an array 714 of transducer elements 716 or alternatively a single transducer element 716 through a surface of the patient 730, such as the skull 728 as illustrated. The array 714 of transducer elements 716 can be configured to be disposed on or near the external surface of the patient's skull 728. The array 714 is configured in a curved shape (e.g., spherical, although sections of other shapes are possible such as planar) conducive for being placed on the patient's head and for focusing ultrasound energy at a distance from the surface of the array 714. The transducer elements 716 of the array 714 are piezoelectric transducer elements arranged in the array 714 as shown. The transducer elements are mounted in silicone rubber or any other material suitable for damping the mechanical coupling between the elements 716. Other materials may also be used for the array construction. For example, the array 714 may be formed from one or more pieces of piezocomposite material, or any material that converts electrical energy to acoustic energy. The amplifier can be in turn operably connected to a frequency generator 722. The array 714 can be optionally coupled to a signal adjuster (not shown) that is further coupled to the frequency generator 722. The frequency generator 722 can be configured to provide a common radio frequency (RF) signal as the input signal to the signal adjuster 718. The radio frequency generator 722 can be of any type that will produce the appropriate signals for the signal adjuster 718. For example, the generator 722 may be a Model DS345 generator available from Stanford Research Systems. Together, the radio frequency generator 722 and signal adjuster 718 are configured to drive the individual transducer elements 716 of the array 714 at the same frequency, but at different phases (and possibly different amplitudes), in order to transmit ultrasound energy through the patient's skull 728 and focus the energy at a selected region within the patient's brain.

In some embodiments, the controller 126 is also configured to manipulate images from the imager 712. The controller 126 can be configured to produce a 3-dimensional rendering of the patient's skull 728 from 2-dimensional images received from the imager 712 and to determine skull thickness from the 3-dimensional rendering. The 3-dimensional rendering can be divided by the controller 126 into voxels (a volume pixel of the 3-dimensional image).

The imager 712 can be configured to obtain images of the interior of the patient's head, and in particular images that provide information regarding thickness, density, and structure of bone of the patient's skull 728. For example, the imager 712 may be a Magnetic Resonance Imaging (MRI) device or Computer Tomography (CT) device. The imager 712 is configured to scan the patient's skull 728 and provide information related to skull thickness, density and structure. This information includes 2-dimensional images of varying intensity from which 3-dimensional renderings can be made and from which thicknesses and densities can be determined and/or inferred. Three-dimensional image acquisition may also be possible and can be used. Also, if the imager 712 is a CT device, the imager 712 can determine and provide the CT number (also called Hounsfield number) for each pixel in images provided by the imager 712.

The ultrasound therapy utilized could be continuous or pulsed depending on the desired result. To perform acoustic therapy, ultrasound elements in the form of acoustic transducers can output acoustic energy at a frequency between about 10 kHz and about 20 MHz. For example, in one embodiment, the acoustic waves have a frequency between about 200 kHz and about 20 MHz. In another embodiment, the waves have a frequency between about 1 MHz and about 3 MHz. In yet another embodiment, the waves have a frequency of about 2 MHz. In some embodiments, the average acoustic power can be between about 0.01 watts and 400 watts.

In one embodiment, the ultrasound non-light energy portion of the multi-modality therapy utilizes a frequency of between about 0.5 MHz and 5 MHz, or between about 1 MHz and 4 MHz in some embodiments. A 1 MHz sound frequency (capable of achieving deep penetration into the brain), and 4 MHz sound frequency, which is the upper frequency that which can be considered for more superficial brain treatment, are examples of frequencies that can be used. In some embodiments, ultrasound systems can operate on a variable frequency to perform therapies at a variety of frequencies. In some embodiments, the primary sound intensity of the ultrasound could be less than about, for example, 1, 0.9, 0.8, 0.7, 0.6, 0.5, 0.4, 0.3, 0.2, 0.1, 0.08, 0.06, 0.04, 0.02, or less W/cm$^2$ depending on the desired clinical result. In some embodiments, the total ultrasound therapy could be administered for less than about 30, 25, 20, 15, 12, 10, 9, 8, 7, 6, 5, 4, 3, 2, or 1 minute, or less than about 50, 40, 30, 20, or 10 seconds in some embodiments. In some embodiments, the ultrasound could be high-intensity (HIFU) or low-intensity ultrasound.

To enhance delivery of energy, one or more transmission media can be applied to the skin. The transmission media can increase the amount of energy reaching the skin, thus increasing the amount of energy ultimately reaching the target site. The transmission media can increase the rate of energy delivery (thereby shortening the treatment period) and the total amount of energy that ultimately reaches the target site possibly improving the efficacy of the therapy session. Transmission media can include, in some embodiments, one or more coupling fluids or gels that facilitate propagation of energy to the patient.

The one or more transmission media can comprise a gel, such as an optical clearing gel (e.g., glycerin gel), suitable for placement between the light energy system and the patient. Other types of transmission media can also be used. For example, transmission media can be designed to transmit non-light energy to the tissue. An acoustic coupling media (e.g., a coupling agent or gel) can be used to ensure good acoustic coupling between an acoustic transducer and the treatment site. Additionally, water, saline, water-based solutions, ultrasound gels or any other suitable transmission media can be used in combination with the transducers and light sources disclosed herein. The transmission media can be spread before and/or during the therapy session. It is contemplated that one or more layers of acoustic coupling gel can be disposed between the patient and any light energy source and/or any non-light energy source.

Thermal Energy and Cooling

In some embodiments, the multimodality therapy includes raising or lowering the temperature of the tissue to be treated compared to body temperature, along with the administration of light therapy as disclosed herein. Possible advantageous clinical applications could include, for example, pain management and treatment of neuropathies, treatment of musculoskeletal conditions such as muscle sprains, strains, ligament and tendon tears, or rheumatological conditions such as fibromyalgia, lupus, or arthritis. In some embodiments, the heating or cooling is delivered externally, such as by way of a hot or cold pack or other thermally conductive element applied to the skin, a thermally controlled air vent, or the like. The heating or cooling could also be delivered via administration of intravenous fluids of a desired temperature into the systemic circulation, into an artery feeding the tissue to be treated, such as an internal or external carotid artery, for example, or locally, such as via lavage into a body cavity, such as the bladder, peritoneum, pleural cavity, or in the skull. In some embodiments, the heating or cooling is delivered in a closed loop containing circulating media, which can be delivered to a target region via a pump. In some embodiments, the temperature of the tissue to be treated is altered, such as reduced, by at least about 1, 2, 3, 4, 5, 6, 7, 8, 9, 10, or more degrees Fahrenheit. In some embodiments, the temperature of the tissue to be treated is altered, such as reduced, by no more than about 1, 2, 3, 4, 5, 6, 7, 8, 9, 10, or less degrees Fahrenheit, depending on the desired clinical result. Thermal devices, such as resistive heaters, can operate on a fixed or variable power mode and can be in thermal communication with the tissue to be treated.

Timing

In some embodiments, the light therapy and the non-light energy therapy can be administered concurrently. When administered concurrently, the light therapy and the non-light energy therapy may partially overlap, that is, one therapy may be administered for a period of time while the other therapy is not being administered, or fully overlap in some embodiments. In some embodiments, the light therapy is administered prior to, or after the other energy modality, such as within about 24 hours, 18 hours, 12 hours, 9 hours, 6 hours, 5 hours, 4 hours, 3 hours, 2 hours, 1 hour, 45 minutes, 30 minutes, 15 minutes, 10 minutes, 5 minutes, 4 minutes, 3 minutes, 2 minutes, 1 minute, or less. In some embodiments, 1, 2, 3, 4, 5, 6, 7, 8, 9, 10 or more cycles of light therapy and another energy modality are utilized.

Figure 3A:
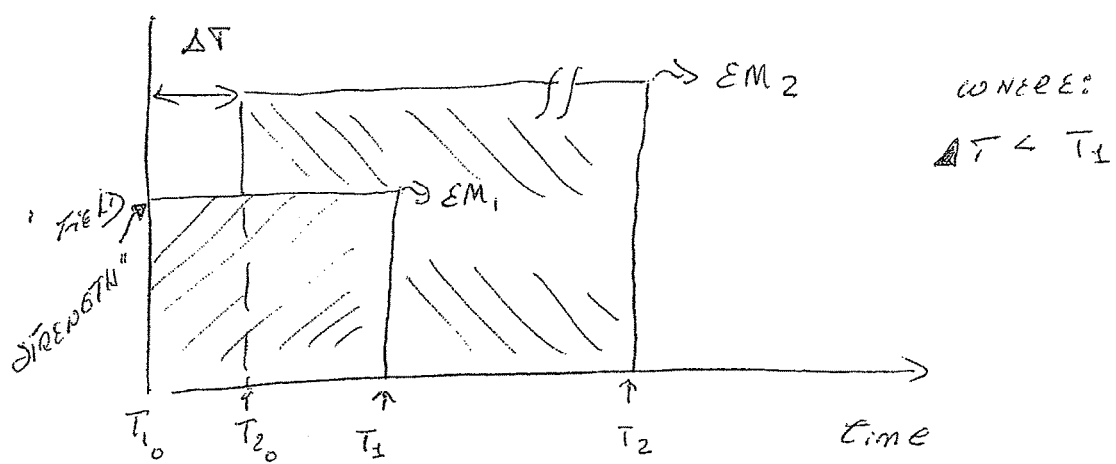
FIGS. 3A-3D schematically illustrate graphs of embodiments of potential energy administration protocols for a plurality of energy sources.
Figure 3B:
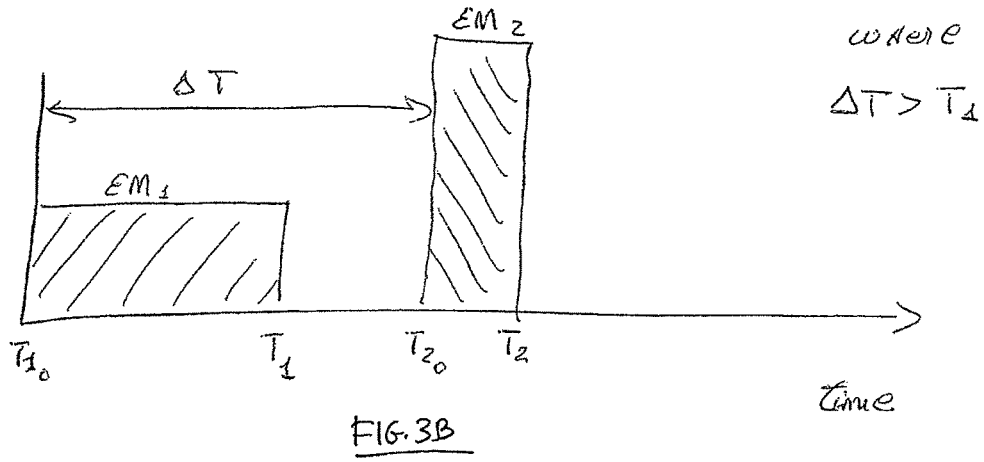
Figure 3C:
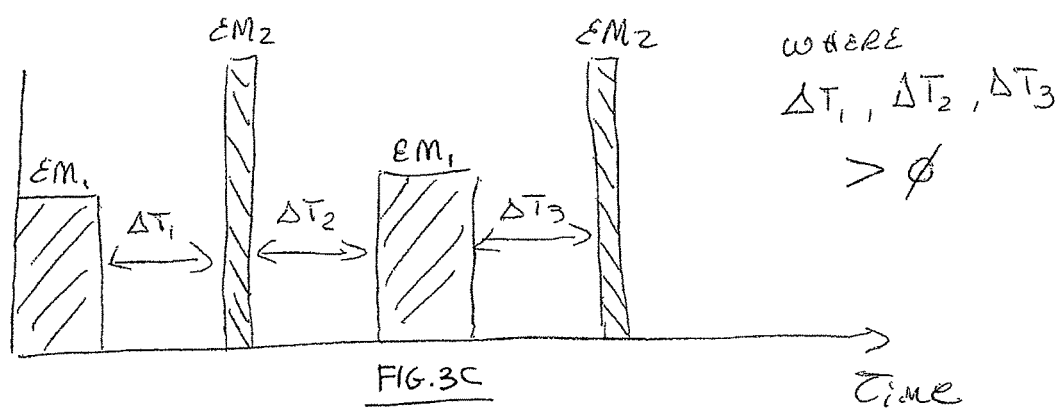
Figure 3D:
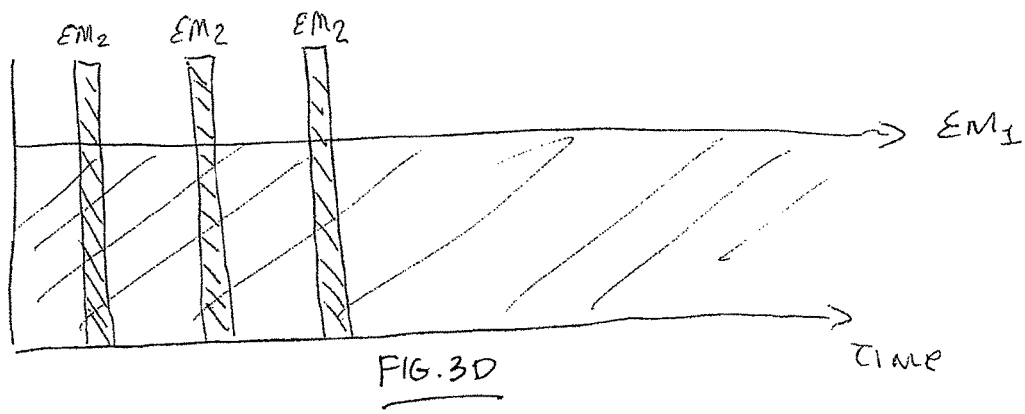

FIGS. 3A-3D illustrate schematically various graphs of embodiments of non-limiting potential administration protocols of a first energy therapy ($EM_1$) and a second energy therapy ($EM_2$), either of which could be light therapy or non-light therapy. The Y axis of the graph could represent power density (or field strength in electromagnetic embodiments), while the X axis is time elapsed. FIG. 3A illustrates a graph of one embodiment of overlapping administration of a first energy therapy ($EM_1$) and a second energy therapy ($EM_2$). FIG. 3B illustrates a graph of non-overlapping administration of a first energy therapy ($EM_1$) followed by a second energy therapy ($EM_2$). FIG. 3C illustrates a graph of one embodiment of interlaced cyclic administration of first energy therapy ($EM_1$) and a second energy therapy ($EM_2$). FIG. 3D illustrates a graph of constant administration of a first energy therapy ($EM_1$) with intermittent overlapping administration of a second energy therapy ($EM_2$). While the graphs of FIGS. 3A-3D illustrate relatively constant power or field strength of each energy therapy during the on-time of each therapy, the power could increase and/or decrease in a gradual, accelerated, decelerated or stepped fashion; undulate (e.g., in a sinusoidal fashion), or otherwise vary for either or both of the first energy therapy ($EM_1$) and the second energy therapy ($EM_2$). Numerous other combinations of administration of a plurality of energy modalities are possible, depending on the desired clinical result. Various examples of quantitative power and time protocols are discussed elsewhere in the application.

Therapeutic Regions

Any desired anatomical region or regions can be treated using the systems and methods described herein, depending on the desired clinical result. Brain tissue may be treated, including one, two, or more of the following regions the insula, subcallosal area, cingulate, prefrontal cerebral cortex, mesial temporal lobe, hypothalamus, hippocampus, amygdala, brain stem, occipital lobe, temporal lobe, frontal lobe, orbitofrontal cortex, parietal lobe, Wernicke's area, area tempestas, basal ganglia, globus pallidus, superior colliculus, striatum, ventral striatum, ventral pallidum, caudate nucleus, putamen, nucleus accumbens, ventral tegmentum, Brodmann areas 24, 25, 32, piriform cortex, ventricular region, ventral pallidum, and forebrain circumventricular organs, reticulate substantia innominata, rostral midbrain, red nucleus, periaqueductal gray, and white matter tracts leading from an aforementioned area or nucleus. Other non-limiting examples of anatomical locations that can be treated include the spinal cord, ocular tissue, bones, including long bones, the bone marrow, lungs, heart, liver, gallbladder, pancreas, kidneys, spleen, bladder, esophagus, stomach, intestines, rectum, anus, reproductive organs, and the like.

Treatment Effects

Beneficial physiological effects may include, without limitation, reduction of pain, improved rate of healing, reduction of inflammation, improved neurologic function, including strength, sensation, vision, hearing, olfactory, taste, cranial nerve function, cognition, gait, and balance, and the like. Other non-limiting possible treatment effects can include enhancement of a number of cell-related activities: cell replication, cell metabolism, protein synthesis, ATP production, mitochondria replication, phagocytosis, and photodissociation of oxygenated hemoglobin. Effects may include, for example: capillary formation, parasympathetic nervous system stimulation, increased endorphin release, increased production and release of adrenal steroids, reduction in pain and in inflammation, reduction of tissue edema, immune system stimulation, enhanced fibroblastic production and collagen synthesis, and accelerated healing of wounds. In some embodiments, a treatment effect could include neuroprotection of ischemic tissue or tissue surrounding the ischemic penumbra. In some embodiments, a beneficial effect could include slowing or preventing the otherwise irreversible loss of neurons due to neurodegeneration after a primary destructive event, whether the neurodegeneration is due to disease mechanisms associated with the primary destructive event or secondary destructive event. In some embodiments, systems and methods as disclosed herein could treat a wide variety of psychiatric conditions or other disorders, including dysthymia, depression, anxiety, bipolar disorder, mania, schizophrenia, schizoaffective disorder, obsessive-compulsive disorder, panic disorder, post-traumatic stress disorder, phobias, anorexia, bulimia, Tourette's syndrome, insomnia, hypersomnia, and others.

Furthermore, with regard to at least light therapy, without being limited by theory, a beneficial effect on mitochondria could be present. The mitochondria convert oxygen and a carbon source to water and carbon dioxide, producing energy (as ATP) and reducing equivalents (redox state) in the process. The chemical energy released from glucose and oxygen is converted to a proton gradient across the inner membrane of the mitochondria. This gradient is, in turn, used by the ATPase complex to make ATP. In addition, the flow of electrons down the electron transfer chain produces NADPH and NADH (and other factors such as FAD). These cofactors are important for maintaining the redox potential inside the cell within the optimal range. This process has been called the chemi-osmotic theory of mitochondrial function.

There are 5 large components of the electron transfer chain, Complexes I-IV and the ATPase (also called Complex V), with each complex containing a number of individual proteins (see FIG. 1). One of the critical complexes, Complex IV (cytochrome oxidase), is the component responsible for the metabolism of oxygen. The cytochrome C oxidase protein is a key player in the electron transfer in Complex IV through its copper centers. These copper centers have been proposed as critical chromophores (photoacceptors) for the absorption of light energy in the near infra-red region. Release of cytochome C oxidase from the mitochondria into the cytosol is a pro-apoptotic signal. It is postulated by Karu that light can directly activate Complex IV and indirectly driving the production of ATP via ATPase (and reducing equivalents). Karu studied the activation spectra of these processes and found that wavelengths that maximally stimulated energy-dependant cellular functions corresponded to the absorption bands of the copper centers in cytochrome C oxidase. Additional data from the Whelan group suggest that cytochrome C oxidase is a potentially important target. Light (e.g., 670 nm) can rescue primary neurons from the toxic effects of the sodium channel blocker tetrodotoxin (TTX). TTX reduces cytochome oxidase activity in treated neurons, and this reduction is reversed by light treatment (an increase in cytochrome oxidase activity). In an in vivo model, 670 nm light is used to rescue retinal function in a methanol-mediated model of retinal damage. Methanol is metabolized to formate, a selective mitochondrial toxin targeted at cytochome C oxidase. Irradiation with light (670 nm) rescued the retina from damage induced by methanol.

As used herein, the term "neurodegeneration" refers to the process of cell destruction resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, epilepsy, Alzheimer's disease, Parkinson's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules (e.g., reactive oxygen species, such as free radicals), including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for neurons, wherein the neurons in the zone have at least temporarily survived the primary destructive event, but are at risk of dying due to processes having delayed effect.

Light Parameters

In some embodiments, the electromagnetic radiation comprises low level light therapy ("LLLT") or phototherapy. Phototherapy involves therapeutic administration of light energy to a patient at lower power outputs than those used for cutting, cauterizing, or ablating biological tissue, resulting in desirable biostimulatory effects while leaving tissue undamaged. In other embodiments, the electromagnetic radiation comprises infrared light. In some embodiments a device may be used to administer at least a portion of the electromagnetic radiation to subdermal tissues. In certain such embodiments, the device comprises parameters for light administration to a patient. Examples of devices for infrared light administration to a patient compatible with certain embodiments described herein are disclosed in U.S. Pat. No. 7,303,578, U.S. Patent Application Publication Nos. 2005/0107851 A1, 2007/0179570 A1, and U.S. patent application Ser. No. 12/389,294, all of which are incorporated in their entireties by reference herein. Further embodiments of devices that can be utilized or adapted for utilization herein are described in U.S. Pat. No. 6,974,224 to Thomas-Benedict and U.S. Pat. Pub. No. 2007/0129776 to Robins et al., both of which are hereby incorporated by reference in their entireties.

It is desirable to apply an efficacious amount of light energy to the internal tissue to be treated using light sources positioned outside the body, as schematically illustrated by FIG. 1. Examples of use of external light energy to treat internal tissues are disclosed in U.S. Pat. Nos. 6,537,304 and 6,918,922, both of which are incorporated in their entireties by reference herein.

The various parameters of the light beam emitted from the emission surface of the light source are advantageously selected to provide treatment while controlling, inhibiting, preventing, minimizing, or reducing injury or discomfort to the patient due to heating of the skin, tissue, or bone by the light. While discussed separately, these various parameters below can be combined with one another within the disclosed values in accordance with embodiments described herein.

Wavelength

In certain embodiments, light in the visible to near-infrared wavelength range is used to irradiate the tissue being treated. In certain embodiments, the light is substantially monochromatic (e.g., light having a narrow band of wavelengths). So that the amount of light transmitted to the tissue being treated is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In certain other embodiments, the light comprises one or more wavelengths between about 630 nanometers and about 1064 nanometers, between about 600 nanometers and about 980 nanometers, between about 780 nanometers and about 840 nanometers, between about 805 nanometers and about 820 nanometers, or includes wavelengths of about 785, 790, 795, 800, 805, 810, 815, 820, 825, or 830 nanometers. An intermediate wavelength in a range between approximately 730 nanometers and approximately 750 nanometers (e.g., about 739 nanometers) may also be suitable for irradiating the tissue being treated, although other wavelengths are also suitable and may be used. In other embodiments, a plurality of wavelengths is used (e.g. applied concurrently or sequentially). In certain embodiments, the light has a wavelength distribution peaked at a peak wavelength and has a linewidth less than ±10 nanometers from the peak wavelength. In certain such embodiments, the light has a linewidth less than 4 nanometers, full width at 90% of energy. In certain embodiments, the center wavelength is (808±10) nanometers with a spectral linewidth les than 4 nanometers, full width at 90% of energy.

In certain embodiments, the light is generated by a light source comprising one or more laser diodes, which each provide coherent light. In embodiments in which the light from the light source is coherent, the emitted light may produce "speckling" due to coherent interference of the light. This speckling comprises intensity spikes which are created by wavefront interference effects and can occur in proximity to the target tissue being treated. For example, while the average irradiance or power density may be approximately 10 mW/cm², the power density of one such intensity spike in proximity to the target tissue to be treated may be less than about 300, 200, 100, 50, 25, 10, or less mW/cm². In certain embodiments, this increased power density due to speckling can improve the efficacy of treatments using coherent light over those using incoherent light for illumination of deeper tissues. In addition, the speckling can provide the increased power density without overheating the tissue being irradiated. The light within the speckle fields or islands containing these intensity spikes is polarized, and in certain embodiments, this polarized light provides enhanced efficacy beyond that for unpolarized light of the same intensity or irradiance.

In certain embodiments, the light source includes at least one continuously emitting GaAlAs laser diode having a wavelength of about 830 nanometers. In another embodiment, the light source comprises a laser source having a wavelength of about 808 nanometers. In still other embodiments, the light source includes at least one vertical cavity surface-emitting laser (VCSEL) diode. Other light sources compatible with embodiments described herein include, but are not limited to, light-emitting diodes (LEDs) and filtered lamps. Other light therapy embodiments are described, for example, in U.S. Pat. No. 5,989,245 to Prescott, U.S. Pat. No. 7,303,578 to de Taboada et al., and U.S. Pat. Pub. No. 2009/0254154 A1 to de Taboada et al., all of which are hereby incorporated by reference in their entireties.

In certain embodiments, the one or more wavelengths are selected so as to work (e.g., cooperate functionally) with one or more chromophores within the target tissue. Without being bound by theory or by a specific mechanism, it is believed that irradiation of mitochondrial chromophores increases the production of ATP in the target tissue and/or controls, inhibits, prevents, minimizes, or reduces apoptosis of the injured tissues, thereby producing beneficial effects, as described more fully below.

Some chromophores, such as water or hemoglobin, are ubiquitous and absorb light to such a degree that little or no penetration of light energy into a tissue occurs. For example, water absorbs light above approximately 1300 nanometers. Thus energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers.

Based on these broad assumptions, one can define an "IR window" into the body. Within the window, there are certain wavelengths that are more or less likely to penetrate. This discussion does not include wavelength dependent scattering effects of intervening tissues.

The absorption/transmittance of various tissues have been directly measured to determine the utility of various wavelengths. For example, blood absorbs less in the region above 700 nanometers, and is particularly transparent at wavelengths above 780 nanometers. Wavelengths below 700 nanometers are heavily absorbed, and are not likely to be useful therapeutically (except for topical indications).

Absorption by the target tissue can be strong in a range of wavelengths (e.g., between 620 and 980 nanometers) at which copper centers in mitochondria absorb. Thus, absorption in the range of wavelengths is expected upon a photostimulative effect taking place.

By combining the transmittance through intervening tissue with the absorption by target tissue, the efficiency of energy delivery as a function of wavelength can be calculated.

Wavelengths between 780 and 880 nanometers are preferable (efficiency of 0.6 or greater) for certain embodiments described herein. The peak efficiency is about 800 to 830 nanometers (efficiency of 1.0 or greater). These wavelengths are not absorbed by water or hemoglobin, and are likely to penetrate to the tissue being treated. Once these wavelengths reach the tissue being treated, they will be absorbed by the cells within the tissue and converted to useful energy.

Irradiance or Power Density

In certain embodiments the light energy has a time averaged irradiance or power density at the emission surface of the light source between about 1 mW/cm² to about 10 W/cm², between about 3 mW/cm² to about 7 W/cm², about 5 W/cm², between about 100 mW/cm² to about 1000 mW/cm², between about 500 mW/cm² to about 1 W/cm², or between about 650 mW/cm² to about 750 mW/cm² across the cross-sectional area of the light beam. In certain embodiments the light energy has a time averaged irradiance or power density at the emission target surface (at the skin) of the light source that is less than about 1 W/cm², 750 mW/cm², 750 mW/cm², 650 mW/cm², 500 mW/cm², 400 mW/cm², 300 mW/cm², 200 mW/cm², 100 mW/cm², 50 mW/cm², 10 mW/cm², 5 mW/cm², 1 mW/cm², or less.

For a pulsed light beam, the time-averaged irradiance is averaged over a time period long compared to the temporal pulse widths of the pulses (e.g., averaged over a fraction of a second longer than the temporal pulse width, over 1 second, or over multiple seconds). For a continuous-wave (CW) light beam with time-varying irradiance, the time-averaged irradiance can be an average of the instantaneous irradiance averaged over a time period longer than a characteristic time period of fluctuations of the light beam. In certain embodiments, a duty cycle in a range between 1% and 80%, between 10% and 30%, or about 20% can be used with a peak irradiance at the emission surface 22 of the output optical assembly 20 between about 12.5 mW/cm² to about 1000 W/cm², between about 50 mW/cm² to about 50 W/cm², between about 500 mW/cm² to about 5000 mW/cm², between about 2500 mW/cm² to about 5 W/cm², or between about 3.25 W/cm² to about 3.75 W/cm² across the cross-sectional area of the light beam. In certain embodiments, the pulsed light beam has an energy or fluence (e.g., peak irradiance multiplied by the temporal pulsewidth) at the emission surface of the light source between about 12.5 µJ/cm² to about 1 J/cm², between about 50 µJ/cm² to about 50 mJ/cm², between about 500 µJ/cm² to about 5 mJ/cm², between about 2.5 mJ/cm² to about 5 mJ/cm², or between about 3.25 mJ/cm² to about 3.75 mJ/cm².

The cross-sectional area of the light beam of certain embodiments (e.g., multimode beams) can be approximated using an approximation of the beam intensity distribution. For example, measurements of the beam intensity distribution can be approximated by a Gaussian ($1/e^2$ measurements) or by a "top hat" distribution and a selected perimeter of the beam intensity distribution can be used to define a bound of the area of the light beam. In certain embodiments, the irradiance at the emission surface of the light source is selected to provide the desired irradiances at the subdermal target tissue. The irradiance of the light beam is preferably controllably variable so that the emitted light energy can be adjusted to provide a selected irradiance at the subdermal tissue being irradiated. In certain embodiments, the light beam emitted from the emission surface of the light source is continuous with a total radiant power in a range of about 4 Watts to about 6 Watts. In some embodiments, the total radiant power is less than about 6, 5, 4, 3, 2, 1 Watt, or even less. In certain embodiments, the radiant power of the light beam is 5 Watts±20% (CW). In certain embodiments, the peak power for pulsed light is in a range of about 10 Watts to about 30 Watts (e.g., 20 Watts), or between about 5 Watts and 10 Watts in some embodiments. In certain embodiments, the peak power for pulsed light multiplied by the duty cycle of the pulsed light yields an average radiant power in a range of about 2 Watts to about 6 Watts (e.g., 5 Watts).

In certain embodiments, the time-averaged irradiance at the subdermal target tissue is at least about 0.01 mW/cm$^2$ and up to about 1 W/cm$^2$ at the level of the tissue. In various embodiments, the time-averaged subsurface irradiance at the target tissue is at least about 0.01, 0.05, 0.1, 0.5, 1, 5, 10, 15, 20, 30, 40, 50, 60, 70, 80, or 90 mW/cm$^2$, depending on the desired clinical performance. In certain embodiments, the time-averaged subsurface irradiance at the target tissue is about 0.01 mW/cm$^2$ to about 100 mW/cm$^2$, about 0.01 mW/cm$^2$ to about 50 mW/cm$^2$, about 2 mW/cm$^2$ to about 20 mW/cm$^2$, or about 5 mW/cm$^2$ to about 25 mW/cm$^2$. In certain embodiments, a duty cycle in a range between 1% and 80%, between 10% and 30%, or about 20% can be used with a peak irradiance at the target tissue of 0.05 mW/cm$^2$ to about 500 mW/cm$^2$, about 0.05 mW/cm$^2$ to about 250 mW/cm$^2$, about 10 mW/cm$^2$ to about 100 mW/cm$^2$, or about 25 mW/cm$^2$ to about 125 mW/cm$^2$. The target tissue could be any desired tissue to be treated, including ischemic brain tissue, and other non-limiting examples of tissue described, for example, elsewhere in the application.

In certain embodiments, the irradiance of the light beam is selected to provide a predetermined irradiance at the subdermal target tissue (e.g., ischemic portions of the brain). The selection of the appropriate irradiance of the light beam emitted from the emission surface of the light source to use to achieve a desired subdermal irradiance preferably includes consideration of scattering by intervening tissue. Further information regarding the scattering of light by tissue is provided by U.S. Pat. No. 7,303,578, V. Tuchin in "Tissue Optics: Light Scattering Methods and Instruments for Medical Diagnosis," SPIE Press (2000), Bellingham, Wash., pp. 3-11, and Wells et al., "Pulsed Laser versus Electrical Energy for Peripheral Nerve Stimulation," J. Neurosci. Methods 163 (2007) 326-327, all of which are incorporated in their entireties by reference herein.

Temporal Pulsewidth, Temporal Pulseshape, Duty Cycle, Repetition Rate, and Irradiance per Pulse In some embodiments, a pulsed light beam is used having a temporal profile comprising a plurality of pulses ($P_1$, $P_2$, ..., $P_i$), each pulse having a temporal pulsewidth during which the instantaneous intensity or irradiance I(t) of the pulse is substantially non-zero. For example, a pulse $P_1$ has a temporal pulsewidth from time t=0 to time t=$T_1$, pulse $P_2$ has a temporal pulsewidth from time t=$T_2$ to time t=$T_3$, and pulse $P_i$ has a temporal pulsewidth from time t=$T_i$ to time t=$T_{i+1}$. The temporal pulsewidth can also be referred to as the "pulse ON time." The pulses are temporally spaced from one another by periods of time during which the intensity or irradiance of the beam is substantially zero. For example, pulse $P_1$ is spaced in time from pulse $P_2$ by a time t=$T_2$-$T_1$. The time between pulses can also be referred to as the "pulse OFF time." In certain embodiments, the pulse ON times of the pulses are substantially equal to one another, while in certain other embodiments, the pulse ON times differ from one another. In certain embodiments, the pulse OFF times between the pulses are substantially equal to one another, while in certain other embodiments, the pulse OFF times between the pulses differ from one another. As used herein, the term "duty cycle" has its broadest reasonable interpretation, including but not limited to, the pulse ON time divided by the sum of the pulse ON time and the pulse OFF time. For a pulsed light beam, the duty cycle is less than one. The values of the duty cycle and the temporal pulsewidth fully define the repetition rate of the pulsed light beam. Further disclosure regarding parameters of pulsed light compatible with certain embodiments described herein may be found in U.S. patent application Ser. No. 12/403,824, filed Mar. 13, 2009, published as U.S. Pub. No. 2009/0254154 A1, which is incorporated in its entirety by reference herein.

Each of the pulses can have a temporal pulseshape which describes the instantaneous intensity or irradiance of the pulse I(t) as a function of time. For example, the temporal pulseshapes of the pulsed light beam may be irregular, and need not be the same among the various pulses. In certain embodiments, the temporal pulseshapes of the pulsed light beam are substantially the same among the various pulses. For example, the pulses can have a square temporal pulseshape, with each pulse having a substantially constant instantaneous irradiance over the pulse ON time. In certain embodiments, the peak irradiances of the pulses differ from one another, while in certain other embodiments, the peak irradiances of the pulses are substantially equal to one another (see, e.g., FIGS. 21A and B, and 21C and D, respectively, of U.S. patent application Ser. No. 12/403,824, filed Mar. 13, 2009, incorporated in its entirety by reference herein). Various other temporal pulseshapes (e.g., triangular, trapezoidal) are also compatible with certain embodiments described herein. For example, FIG. 21C of U.S. patent application Ser. No. 12/403,824, filed Mar. 13, 2009, which is incorporated in its entirety by reference herein, schematically illustrates a plurality of trapezoidal pulses in which each pulse has a rise time (e.g., corresponding to the time between an instantaneous irradiance of zero and a peak irradiance of the pulse) and a fall time (e.g., corresponding to the time between the peak irradiance of the pulse and an instantaneous irradiance of zero). In certain embodiments, the rise time and the fall time can be expressed relative to a specified fraction of the peak irradiance of the pulse (e.g., time to rise/fall to 50% of the peak irradiance of the pulse).

As used herein, the term "peak irradiance" of a pulse $P_i$ has its broadest reasonable interpretation, including but not limited to, the maximum value of the instantaneous irradiance I(t) during the temporal pulsewidth of the pulse. In certain embodiments, the instantaneous irradiance is changing during the temporal pulsewidth of the pulse while in certain other embodiments, the instantaneous irradiance is substantially constant during the temporal pulsewidth of the pulse.

As used herein, the term "pulse irradiance" $I_{P_i}$ of a pulse $P_i$ has its broadest reasonable interpretation, including but not limited to, the integral of the instantaneous irradiance I(t) of the pulse $P_i$ over the temporal pulsewidth of the pulse:

$$I_{P_i} = \int_{T_i}^{T_{i+1}} I(t) \cdot dt / (T_{i+1} - T_i).$$

As used herein, the term "total irradiance" $I_{TOTAL}$ has its broadest reasonable interpretation, including but not limited to, the sum of the pulse irradiances of the pulses:

$$I_{TOTAL} = \sum_{i=0}^{N} I_{P_i}.$$

As used herein, the term "time-averaged irradiance" $I_{AVE}$ has its broadest reasonable interpretation, including but not limited to, the integral of the instantaneous irradiance I(t) over a period of time T large compared to the temporal pulsewidths of the pulses:

$$I_{AVE} = \int_0^T I(t) \cdot dt / T.$$

The integral $$\int_0^T I(t) \cdot dt$$

provides the energy of the pulsed light beam.

For example, for a plurality of square pulses with different pulse irradiances $I_{P_i}$ and different temporal pulsewidths $\Delta T_i$, the time-averaged irradiance over a time T equals $$I_{AVE} = \frac{1}{T} \sum_i I_{P_i} \cdot \Delta T_i.$$

For another example, for a plurality of square pulses with equal pulse irradiances $I_P$, with equal temporal pulsewidths, and equal pulse OFF times (having a duty cycle D), the time-averaged irradiance equals $I_{AVE}=I_P \cdot D$. For example, as shown in FIG. 21D of U.S. patent application Ser. No. 12/403,824, the time-averaged irradiance (shown as a dashed line) is less than the pulse irradiance of the pulses.

The pulse irradiances and the duty cycle can be selected to provide a predetermined time-averaged irradiance. In certain embodiments in which the time-averaged irradiance is equal to the irradiance of a continuous-wave (CW) light beam, the pulsed light beam and the CW light beam have the same number of photons or flux as one another. For example, a pulsed light beam with a pulse irradiance of 5 mW/cm$^2$ and a duty cycle of 20% provides the same number of photons as a CW light beam having an irradiance of 1 mW/cm$^2$. However, in contrast to a CW light beam, the parameters of the pulsed light beam can be selected to deliver the photons in a manner which achieve results which are not obtainable using CW light beams.

For example, for hair removal, tattoo removal, or wrinkle smoothing, pulsed light beams have previously been used to achieve selective photothermolysis in which a selected portion of the skin is exposed to sufficiently high temperatures to damage the hair follicles (e.g., temperatures greater than 60 degrees Celsius), to ablate the tattoo ink (e.g., temperatures much greater than 60 degrees Celsius), or to shrink the collagen molecules (e.g., temperatures between 60-70 degrees Celsius), respectively, while keeping the other portions of skin at sufficiently low temperatures to avoid unwanted damage or discomfort. The parameters of these pulsed light beams are selected to achieve the desired elevated temperature at the selected portion of the skin by absorption of the light by the selected chromophore while allowing heat to dissipate (characterized by a thermal relaxation time) during the pulse OFF times to keep other areas of skin at lower temperatures. As described by J. Lepselter et al., "Biological and clinical aspects in laser hair removal," J. Dermatological Treatment, Vol. 15, pp. 72-83 (2004), the pulse ON time for hair removal is selected to be between the thermal relaxation time for the epidermis (about 3-10 milliseconds) and the thermal relaxation time for the hair follicle (about 40-100 milliseconds). In this way, the hair follicle can be heated to sufficiently high temperatures to damage the follicle without causing excessive damage to the surrounding skin.

In contrast to these treatments which are based on creating thermal damage to at least a portion of the skin, certain embodiments described herein utilize pulse parameters which do not create thermal damage to at least a portion of the skin. In certain embodiments, one or more of the temporal pulsewidth, temporal pulseshape, duty cycle, repetition rate, and pulse irradiance of the pulsed light beam are selected such that no portion of the skin is heated to a temperature greater than 60 degrees Celsius, greater than 55 degrees Celsius, greater than 50 degrees Celsius, or greater than 45 degrees Celsius. In certain embodiments, one or more of the temporal pulsewidth, temporal pulseshape, duty cycle, repetition rate, and pulse irradiance of the pulsed light beam are selected such that no portion of the skin is heated to a temperature greater than 30 degrees Celsius above its baseline temperature, greater than 20 degrees Celsius above its baseline temperature, or greater than 10 degrees Celsius above its baseline temperature. In certain embodiments, one or more of the temporal pulsewidth, temporal pulseshape, duty cycle, repetition rate, and pulse irradiance of the pulsed light beam are selected such that no portion of the bone marrow is heated to a temperature greater than 5 degrees Celsius above its baseline temperature, greater than 3 degrees Celsius above its baseline temperature, or greater than 1 degree Celsius above its baseline temperature. As used herein, the term "baseline temperature" has its broadest reasonable interpretation, including but not limited to, the temperature at which the tissue would have if it were not irradiated by the light. In contrast to previous low-light level therapies, the pulsed light beam has an average radiant power in the range of about 1 Watt to about 6 Watts or in a range of about 4 Watt to about 6 Watts.

A number of studies have investigated the effects of in vitro irradiation of cells using pulsed light on various aspects of the cells. A study of the action mechanisms of incoherent pulsed radiation at a wavelength of 820 nanometers (pulse repetition frequency of 10 Hz, pulse width of 20 milliseconds, dark period between pulses of 80 milliseconds, and duty factor (pulse duration to pulse period ratio) of 20%) on in vitro cellular adhesion has found that pulsed infrared radiation at 820 nanometers increases the cell-matrix attachment. (T. I. Karu et al., "*Cell Attachment to Extracellular Matrices is Modulated by Pulsed Radiation at* 820 *nm and Chemicals that Modify the Activity of Enzymes in the Plasma Membrane*," Lasers in Surgery and Medicine, Vol. 29, pp. 274-281 (2001) which is incorporated in its entirety by reference herein.) It was hypothesized in this study that the modulation of the monovalent ion fluxes through the plasma membrane, and not the release of arachidonic acid, is involved in the cellular signaling pathways activated by irradiation at 820 nanometers. A study of light-induced changes to the membrane conductance of ventral photoreceptor cells found behavior which was dependent on the pulse parameters, indicative of two light-induced membrane processes. (J. E. Lisman et al., "*Two Light-Induced Pro-* cesses in the Photoreceptor Cells of Limulus Ventral Eye," J. Gen. Physiology, Vol. 58, pp. 544-561 (1971), which is incorporated in its entirety by reference herein.) Studies of laser-activated electron injection into oxidized cytochrome c oxidase observed kinetics which establish the reaction sequence of the proton pump mechanism and some of its thermodynamic properties have time constants on the order of a few milliseconds. (I. Belevich et al., "*Exploring the proton pump mechanism of cytochrome c oxidase in real time*," Proc. Nat'l Acad. Sci., Vol. 104, pp. 2685-2690 (2007); I. Belevich et al., "*Proton-coupled electron transfer drives the proton pump of cytochrome c oxidase*," Nature, Vol. 440, pp. 829-832 (2006), both of which are incorporated in its entirety by reference herein.) An in vivo study of neural activation based on pulsed infrared light proposed a photo-thermal effect from transient tissue temperature changes resulting in direct or indirect activation of transmembrane ion channels causing propagation of the action potential. (J. Wells et al., "*Biophysical mechanisms responsible for pulsed low-level laser excitation of neural tissue*," Proc. SPIE, Vol. 6084, pp. 60840X (2006), which is incorporated in its entirety by reference herein.)

In certain embodiments, the temporal profile of the pulsed light beam comprises a peak irradiance, a temporal pulse width, a temporal pulse shape, a duty cycle, and a pulse repetition rate or frequency. In certain embodiments in which the pulsed light beam is transmitted through a region of tissue containing excess fluid or cellular material (e.g. from swelling induced by glucocorticoids or other drug therapies), at least one of the peak irradiance, temporal pulse width, temporal pulse shape, duty cycle, and pulse repetition rate or frequency is selected to provide a time-averaged irradiance (averaged over a time period including a plurality of pulses) at the surface of the light source, surface of the skin, or surface of the target tissue is between about 10 $mW/cm^2$ to about 10 $W/cm^2$, between about 100 $mW/cm^2$ to about 1000 $mW/cm^2$, between about 500 $mW/cm^2$ to about 1 $W/cm^2$, or between about 650 $mW/cm^2$ to about 750 $mW/cm^2$ across the cross-sectional area of the light beam.

In certain embodiments, the peak irradiance per pulse across the cross-sectional area of the light beam at the emission surface of the light source is in a range between about 10 $mW/cm^2$ to about 10 $W/cm^2$, between about 100 $mW/cm^2$ to about 1000 $mW/cm^2$, between about 500 $mW/cm^2$ to about 1 $W/cm^2$, between about 650 $mW/cm^2$ to about 750 $mW/cm^2$, between about 20 $mW/cm^2$ to about 20 $W/cm^2$, between about 200 $mW/cm^2$ to about 2000 $mW/cm^2$, between about 1 $W/cm^2$ to about 2 $W/cm^2$, between about 1300 $mW/cm^2$ to about 1500 $mW/cm^2$, between about 1 $W/cm^2$ to about 1000 $W/cm^2$, between about 10 $W/cm^2$ to about 100 $W/cm^2$, between about 50 $W/cm^2$ to about 100 $W/cm^2$, or between about 65 $W/cm^2$ to about 75 $W/cm^2$. In certain embodiments, the temporal pulse shape is generally rectangular, generally triangular, or any other shape. In certain embodiments, the pulses have a rise time (e.g., from 10% of the peak irradiance to 90% of the peak irradiance) less than 1% of the pulse ON time, or a fall time (e.g., from 90% of the peak irradiance to 10% of the peak irradiance) less than 1% of the pulse ON time.

In certain embodiments, the pulses have a temporal pulsewidth (e.g., pulse ON time) in a range between about 0.001 millisecond and about 150 seconds, between about 0.01 millisecond and about 10 seconds, between about 0.1 millisecond and about 1 second, between about 0.5 millisecond and about 100 milliseconds, between about 2 milliseconds and about 20 milliseconds, or between about 1 millisecond and about 10 milliseconds. In certain embodiments, the pulse width is about 0.5, 1, 2, 4, 6, 8, 10, 15, 20, 30, 40, 50, 60, 70, 80, 90, 100, 120, 140, 160, 180, 200, 220, 240, 260, 280, or 300 milliseconds. In certain embodiments, the temporal pulsewidth is in a range between about 0.1 millisecond and 150 seconds.

In certain embodiments, the time between pulses (e.g., pulse OFF time) is in a range between about 0.01 millisecond and about 150 seconds, between about 0.1 millisecond and about 100 millisecond, between about 4 milliseconds and about 1 second, between about 8 milliseconds and about 500 milliseconds, between about 8 milliseconds and about 80 milliseconds, or between about 10 milliseconds and about 200 milliseconds. In certain embodiments, the time between pulses is about 4, 8, 10, 20, 50, 100, 200, 500, 700, or 1000 milliseconds.

In certain embodiments, the pulse duty cycle is in a range between about 1% and about 80% or in a range between about 10% and about 30%. In certain embodiments, the pulse duty cycle is about 1%, 2%, 3%, 5%, 7%, 10%, 20%, 30%, 40%, 50%, 60%, 70%, 80%, or 90%.

Beam Size and Beam Profile

In certain embodiments, the light beam will be manipulated (e.g. with non-transmissive materials) to yield a rectangular, oval, or other geometric shape in the approximate length and width of the particular tissue to be irradiated. In certain embodiments, multiple light sources can be used to irradiate the tissue to be treated.

In certain embodiments, the light beam has a nominal diameter in a range of about 10 millimeters to about 40 millimeters, in a range of about 20 millimeters to about 35 millimeters, less than 33 millimeters, or equal to about 30 millimeters. In certain embodiments, the cross-sectional area is generally circular with a radius in a range of about 1 centimeter to about 2 centimeters. In certain embodiments, the light beam irradiating the skin has a cross-sectional area greater than about 2 $cm^2$ or in a range of about 2 $cm^2$ to about 20 $cm^2$ (e.g., at an emission surface of an optical element generating the light beam).

As used herein, the beam diameter is defined to be the largest chord of the perimeter of the area of the skin irradiated by the light beam at an intensity of at least $1/e^2$ of the maximum intensity of the light beam. The perimeter of the light beam used to determine the diameter of the beam is defined in certain embodiments to be those points at which the intensity of the light beam is $1/e^2$ of the maximum intensity of the light beam. The maximum-useful diameter of certain embodiments is limited by the size of the tissue to be irradiated and by the heating of the patient's body by the irradiation. The minimum-useful diameter of certain embodiments is limited by heating and by the total number of treatment sites that could be practically implemented. For example, to cover a large area of one of the patient's tissue to be irradiated with a beam having a small beam diameter would correspondingly use a large number of treatment sites. In certain embodiments, the time of irradiation per treatment site can be adjusted accordingly to achieve a desired exposure dose.

Specifying the total flux inside a circular aperture with a specified radius centered on the exit aperture ("encircled energy") is a method of specifying the power (irradiance) distribution over the light beam emitted from the emission surface of a light source. The "encircled energy" can be used to ensure that the light beam is not too concentrated, too large, or too small. In certain embodiments, the light beam emitted from the emission surface has a total radiant power, and the light beam has a total flux inside a 20-millimeter diameter cross-sectional circle centered on the light beam at the emission surface which is no more than 75% of the total radiant power. In certain such embodiments, the light beam has a total flux inside a 26-millimeter diameter cross-sectional circle centered on the light beam at the emission surface 22 which is no less than 50% of the total radiant power.

In certain embodiments, the beam intensity profile has a semi-Gaussian profile, while in certain other embodiments, the beam intensity profile has a "top hat" profile. In certain embodiments, the light beam is substantially without high flux regions or "hot spots" in the beam intensity profile in which the local flux, averaged over a 3 millimeter by 3 millimeter area, is more than 10% larger than the average flux. Certain embodiments employ a light beam substantially without hot spots, thereby avoiding large temperature gradients at the patient's skin which would otherwise cause discomfort to the patient.

Divergence

In certain embodiments, the beam divergence emitted from the emission surface of the light source is significantly less than the scattering angle of light inside the body tissue being irradiated, which is typically several degrees. In certain embodiments, the light beam has a divergence angle greater than zero and less than 35 degrees.

Treatment time

In certain embodiments, the treatment (light, non-light, or both) per treatment site proceeds continuously for a period of about 1 second to about 2 hours, for a period of about 1 to about 10 minutes, or for a period of about 1 to 5 minutes. For example, the treatment time per treatment site in certain embodiments is about two minutes. In other embodiments, the light energy is delivered for at least one treatment period of at least about five minutes, or for at least one treatment period of at least ten minutes. The minimum treatment time of certain embodiments can be limited by the biological response time (which is on the order of microseconds). The maximum treatment time of certain embodiments is limited by heating and by practical treatment times (e.g., completing treatment prior to or between other treatment regimens). The light energy can be pulsed during the treatment period or the light energy can be continuously applied during the treatment period. If the light is pulsed, the pulses can be 2 milliseconds long and occur at a frequency of 100 Hz, although longer pulselengths and lower frequencies can be used, or at least about 10 nanosecond long and occur at a frequency of up to about 100 kHz.

In certain embodiments, the treatment may be terminated after one treatment period (also referred to herein as a treatment session), while in other embodiments, the treatment may be repeated for at least two, three, four, five, ten, or even more treatment periods. The time between subsequent treatment periods can be at least about five minutes, at least two in a 24-hour period, at least about 1 to 2 days, or at least about one week. The length of treatment time and frequency of treatment periods can depend on several factors, including the functional recovery of the patient. In certain embodiments, one or more treatment parameters can be adjusted in response to a feedback signal from a device (e.g., magnetic resonance imaging) monitoring the patient.

Feedback

Figure 4:
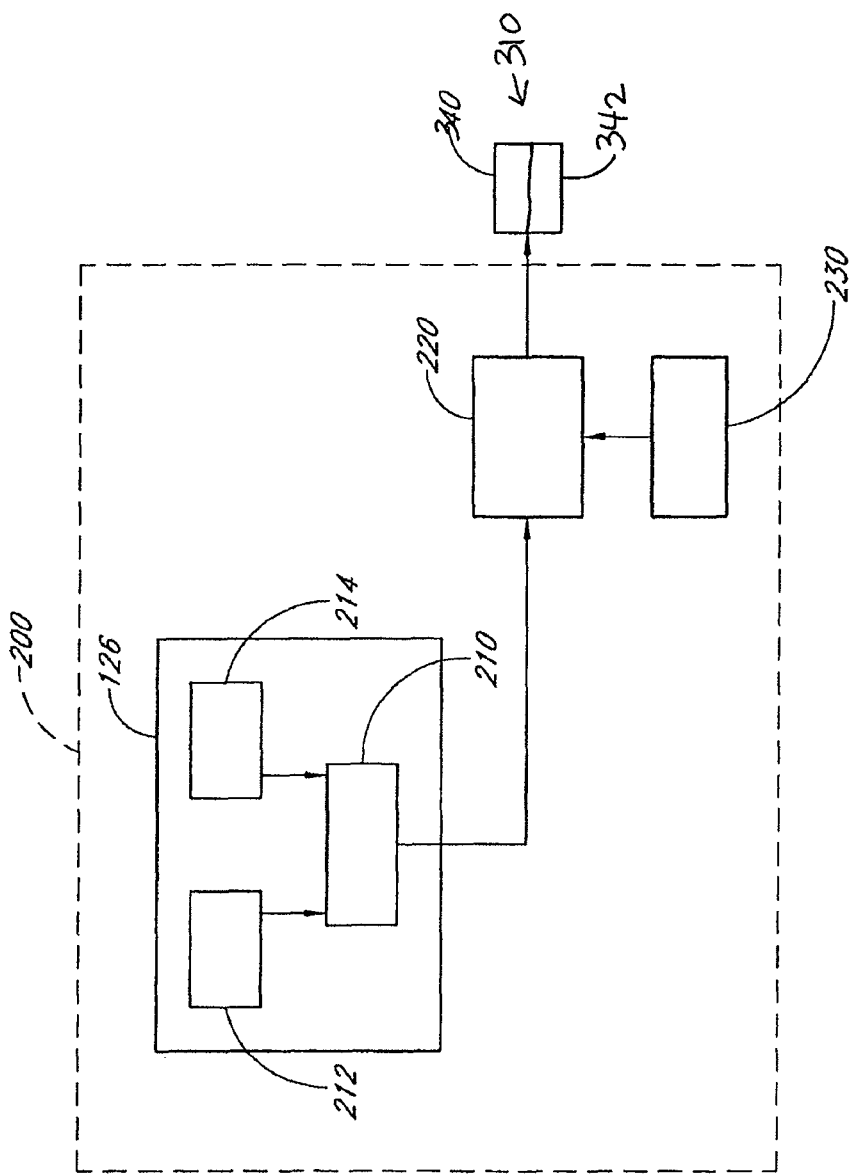
FIG. 4 is a block diagram of a control circuit for controlling one or more energy sources, in accordance with certain embodiments described herein.

FIG. 4 is a block diagram of a control circuit 200 comprising a programmable controller 126 for controlling a light source 340 and/or non-light energy source 342 according to certain embodiments described herein. The control circuit 200 can be configured to adjust the power of the light energy generated by the light source 340 such that the light emitted from the emission surface 122 generates a predetermined surface irradiance at the skull or vertebra corresponding to a predetermined energy delivery profile, such as a predetermined subsurface irradiance, to the target tissue, for example, a target area of the brain. Similarly, the control circuit 200 can be configured to adjust the power or other parameters, as mentioned elsewhere in the application, of the non-light energy source 342. If the non-light energy source 342 is a magnetic energy source, for example, the control circuit 200 could be configured to adjust the magnetic field strength, power density, frequency, or other parameters. In some embodiments, the light source 340 and non-light energy source 342 could be controlled by a single controller, or a plurality of controllers, with each controller controlling a particular energy source.

In certain embodiments, the programmable controller 126 comprises one, two, or more logic circuits 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light and non-light energy. Examples of timing intervals include, but are not limited to, total treatment times, pulse width times for pulses of applied light and non-light energy, and time intervals between pulses of applied light and non-light energy. In certain embodiments, the light source 340 can be selectively turned on and off to reduce the thermal load on the skull or neural tissue and to deliver a selected irradiance to particular areas of the brain or other neural tissue. The non-light energy source 342 can be similarly adjusted. If one or more of the non-light energy sources 342 is configured to be implanted within the patient, the implanted non-light energy source 342 could have a discrete controller, or communicate with a controller external to the patient wirelessly, for example.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied irradiances, target time intervals, and irradiance/timing profiles for the applied light, or power or other measurements for the non-light energy.

In certain embodiments, the logic circuit 210 is coupled to a driver 220 for driving the light and/or non-light energy. The energy source driver 220 is coupled to a power supply 230, which in certain embodiments comprises a battery or capacitive energy storage device and in other embodiments comprises an alternating current source. The energy source driver 220 is also coupled to the light source 340 and/or non-light energy source 342. The logic circuit 210 is responsive to the signal from the clock 212 and to user input from the user interface 214 to transmit a control signal to the driver 220. In response to the control signal from the logic circuit 210, the driver 220 adjusts and controls the power applied to the light source 340 and the non-light energy source 342. Other control circuits besides the control circuit 200 of FIG. 4 are compatible with embodiments described herein. In some embodiments, the control circuit 200 can be used to provide real-time positive and/or negative feedback.

In certain embodiments, the logic circuit 210 is responsive to signals from a sensor monitoring at least one parameter of the treatment to control the applied light and/or non-light energy. For example, certain embodiments comprise a temperature sensor in thermal communication with a body structure, such as the scalp or skull to provide information regarding the temperature of the scalp or skull to the logic circuit 210. In such embodiments, the logic circuit 210 is responsive to the information from the temperature sensor to transmit a control signal to the driver 220 so as to adjust the parameters of the applied light and/or other energy to maintain the scalp or skull temperature below a predetermined level. Other embodiments of sensors include other biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. For example, if ATP production or mitochondrial activity levels are below a certain threshold level, the logic circuit 210 can generate a control signal to the light source 340 or non-light energy source 342 to adjust a treatment parameter of the applied light (such as a treatment time, wavelength, irradiance level, or other parameter) or of the non-light energy. In certain such embodiments, the logic circuit 210 is responsive to signals from the sensors to preferably adjust the parameters of the applied energy to optimize the measured response. The logic circuit 210 can thus provide automatic real-time closed-loop monitoring and adjustment of various parameters of the applied energy to optimize the combination therapy. In other embodiments, the control circuit 200 can be configured to provide manual closed-loop feedback. The sensors can also include biochemical sensors, EEG sensors, EROS sensors, photosensors, and/or other sensors.

Programmable Controller

To tailor one or more of the light or non-light energy emission, energy intensity, energy duration, frequency, area or sequence of application of light and non-light energy to a patient's neural or other tissue, or other treatment parameters, several embodiments comprise a programmable controller 126. In general, the programmable controller 126 executes a set of program instructions that are stored in memory to accomplish tasks or operations such as, but not limited to, operating the one or more light energy sources 340 and non-light energy sources 342 according to a particular therapeutic regimen, communicating with external devices, monitoring the condition of elements such as the light energy sources 340 and non-light energy sources 342 and the power source 230, storing parameters or program instructions in the memory, and the like. For example, the programmable controller 126 can be used to transmit control signals to the driver 220, which responds by driving the light energy source 340 and the non-light energy 342 to transmit light and non-light energy to specific target regions of the brain according to a therapeutic regimen. For example, the programmable controller 126 can execute a treatment program that includes a set of activation times or periods during which each of the light and non-light energy sources is in an emitting state and a set of inactivation times or periods during which the light and non-light energy sources is in a non-emitting state. In certain embodiments, the programmable controller 126 comprises a general or a special purpose microprocessor. The programmable controller 126 can comprise an application-specific integrated circuit (ASIC) or Field Programmable Gate Array (FPGA).

The programmable controller 126 can communicate with internal memory to retrieve and/or store data and/or program instructions for software and/or hardware. In certain embodiments, the programmable controller 126 comprises a central processing unit (CPU). The programmable controller 126 can further include memory, such as random access memory (RAM) for temporary storage of information and/or flash memory, read only memory (ROM), EPROM memory, and/or EEPROM memory for permanent storage of information. In certain embodiments, the memory can be reprogrammable after the initial programming. Additionally, the programmable controller 126 can include a real time clock, one or more timers, an analog to digital (A/D) converter, a digital to analog (D/A) converter, a serial communications interface, such as $I^2C$ or Serial Peripheral Interface, a communications interface, and/or a pulse width modulation (PWM) generator. As depicted in FIG. 5, the power source 230 can provide power to the programmable controller 126, which in turn can drive the one or more light energy sources 340 and non-light energy sources 342. In certain embodiments, the programmable controller 126 drives the one or more energy sources through one, two, or more energy source drivers (not shown) which can be part of the programmable controller 126, part of the energy source 340, 342, or operationally coupled to both the programmable controller 127 and the energy sources 340, 342. The energy source driver can provide an appropriate current or voltage level to energize the one or more energy sources 340, 342. When the programmable controller 126 generates a control signal to drive an energy source 340, 342, energy, (e.g., light energy 50*a*) is emitted from the energy source 340, 342. In contrast, when the energy source 340, 342 is not receiving a control signal from the programmable controller 126 to generate energy, the energy source 340, 342 is in a non-emitting state. The energy sources 340, 342 can be configured to emit energy continuously or periodically in accordance with various therapeutic regimens.

In some embodiments, the programmable controller 126 is preprogrammed (e.g., prior to implantation) with a desired set of treatment parameters for a given patient. For example, a desired frequency of energy emission (e.g., every 24 hours), duration of energy emission (e.g., for 20 minutes), irradiance of energy emission (e.g., from about 1 mW to about 10 mW), irradiation pattern or order of energy source activity (e.g., a sequence of emission of light and non-light energy), and other parameters can be preprogrammed into the programmable controller 126. For pulsed light dosimetry, the treatment parameters can also include duty cycle, pulse shape, repetition rate, pulse width and/or irradiance per pulse for pulsed light dosimetry.

In embodiments comprising a plurality of energy sources, the programmable controller 126 can be programmed to activate a subset of the energy sources to focus on a particular target region. In other embodiments, the programmable controller 126 can be programmed to activate the energy sources according to a predetermined treatment regimen, order, template, or sequence. For example, the treatment regimen can follow a pattern similar to the sequences described in paragraphs [0203]-[0206] of U.S. patent application Ser. No. 12/403,824, the entire contents of which are hereby expressly incorporated by reference herein. The treatment regimen can also be adjustable by a physician (e.g., via telemetry or a wireless and/or wired network interface).

In other embodiments, the programmable controller 126 can be reprogrammed dynamically via the communications interface. The communications interface can comprise an antenna configured to receive RF communication from an external telemetry unit. The communications interface can also be configured to transmit information to the external telemetry unit. Other types of wireless communication links can also be used without departing from the spirit and/or scope of the disclosure. For example, treatment parameters of the phototherapy can be adjusted after implantation in order to optimize the phototherapy based on observed patient response to prior treatments or to adjust the therapy based on a change of conditions or to account for individual patient characteristics. In other embodiments, a physician can adjust treatment parameters in response to an alarm or warning generated by the light therapy apparatus. The physician can reprogram the programmable controller 126 wirelessly via the communications interface.

In still other embodiments, the programmable controller 126 can automatically reprogram itself and/or recalibrate its treatment parameters in response to control signals received from feedback sensors. The sensors can provide feedback regarding the parameters of the light treatment and/or the physiological parameters of the patient. The sensors can include biomedical sensors, biochemical sensors, temperature sensors, and the like. In some embodiments, the sensors can be invasive sensors and can be implanted within the body at least temporarily. In other embodiments, the sensors can comprise noninvasive or minimally invasive sensors. The sensors can be used to measure, for example, adenosine triphosphate (ATP) levels or activity, brain waves (e.g., using an electroencephalography (EEG) sensor system), mitochondrial activity (e.g., by measuring NADH or NADPH levels), nitric oxide (NO) production or consumption, serotonin (5-HT) or selective serotonin reuptake inhibitor (S SRI) activity, cytokines (such as IL-6 interleukins and tumor necrosis factors (TNF)), apoptotic markers (such as Bax and Bcl-2), evoked response optical scanning (EROS) responses, oxygen consumption levels, membrane potential, cholinergic molecule concentration, glycolysis activity, and/or pH levels. For example, increases in cellular ATP concentration and a more reduced state within the cell are both related to cellular metabolism and are considered to be indications that the cell is viable and healthy. The increased concentration of NADH within the targeted neural tissue and a corresponding improvement in the redox state of the targeted neural tissue reflects both the metabolic activities and the health of cells.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially and the individual components of the devices may be combined permanently or be designed for removable attachment at the clinical site. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present invention herein disclosed should not be limited by the particular disclosed embodiments described above.

What is claimed is:

1. A method for treating a patient's brain, comprising:
   administering, to a target tissue of the patient's brain, an amount of light energy; and
   administering, to the target tissue of the patient's brain, an amount of non-light energy, wherein the amount of non-light energy is a subtherapeutic amount of energy,
   wherein the administrations of the amount of light energy and the amount of non-light energy occur within 24 hours of each other,
   wherein the administrations of the amount of light energy and the amount of non-light energy produce a combined treatment effect to the patient that is greater than a sum of: (i) a treatment effect produced by administering the amount of light energy alone plus (ii) a treatment effect produced by administering the amount of non-light energy alone, and
   wherein the time-averaged irradiance of the amount of light energy at the target tissue of the patient's brain is less than 100 mW/cm$^2$.

2. The method of claim 1, wherein the amount of light energy and the amount of non-light energy are administered concurrently.

3. The method of claim 1, wherein the non-light energy is magnetic energy.

4. The method of claim 3, wherein the administering the amount of non-light energy comprises trans-cranial magnetic stimulation.

5. The method of claim 1, wherein the light energy has a wavelength between 630 nanometers to 1064 nanometers.

6. The method of claim 1, wherein the light energy has a wavelength between 730 nanometers to 840 nanometers.

7. The method of claim 1, wherein the light energy has a wavelength between 730 nanometers and 750 nanometers.

8. The method of claim 1, wherein the amount of light energy and the amount of non-light energy are delivered in alternating pulses.

9. A method for treating a patient's brain, comprising:
   administering, to a target tissue of the patient's brain, an amount of light energy; and
   administering, to the target tissue of the patient's brain, an amount of non-light energy,
   wherein the amount of non-light energy is a subtherapeutic amount of energy,
   wherein the administration of the amount of light energy and the amount of non-light energy occur within 24 hours of each other, and
   wherein the administrations of the amount of light energy and the amount of non-light energy produce a combined treatment effect to the patient that is greater than a sum of: (i) a treatment effect produced by administering the amount of light energy alone plus (ii) a treatment effect produced by administering the amount of non-light energy alone.

10. The method of claim 9, wherein the combined treatment effect comprises improvement of neurologic function.

11. The method of claim 9, wherein the amount of light energy and the amount of non-light energy are administered concurrently.

12. The method of claim 9, wherein the non-light energy is magnetic energy.

13. The method of claim 9, wherein the light energy has a wavelength between 630 nanometers to 1064 nanometers.

14. The method of claim 9, wherein the light energy has a wavelength between 730 nanometers to 840 nanometers.

15. The method of claim 9, wherein the light energy has a wavelength between 730 nanometers and 750 nanometers.

16. The method of claim 9, wherein the amount of light energy and the amount of non-light energy are delivered in alternating pulses.

* * * * *